(12) United States Patent
Dicarlo et al.

(10) Patent No.: US 12,311,113 B2
(45) Date of Patent: May 27, 2025

(54) SOFTWARE AND METHODS FOR CONTROLLING NEURAL RESPONSES IN DEEP BRAIN REGIONS

(71) Applicant: Massachusetts Institute of Technology, Cambridge, MA (US)

(72) Inventors: James Dicarlo, Cambridge, MA (US); Pouya Bashivan, Cambridge, MA (US); Kohitij Kar, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 18/482,806

(22) Filed: Oct. 6, 2023

(65) Prior Publication Data

US 2024/0082534 A1  Mar. 14, 2024

Related U.S. Application Data

(62) Division of application No. 16/863,781, filed on Apr. 30, 2020, now Pat. No. 11,813,406.

(60) Provisional application No. 62/841,445, filed on May 1, 2019.

(51) Int. Cl.
*A61M 21/00* (2006.01)
*A61B 5/00* (2006.01)
*A61B 5/378* (2021.01)
*A61B 5/388* (2021.01)
*A61B 5/24* (2021.01)

(52) U.S. Cl.
CPC ............ *A61M 21/00* (2013.01); *A61B 5/378* (2021.01); *A61B 5/388* (2021.01); *A61B 5/7264* (2013.01); *A61B 5/24* (2021.01); *A61B 2562/028* (2013.01); *A61M 2021/005* (2013.01); *A61M 2230/10* (2013.01); *A61M 2250/00* (2013.01)

(58) Field of Classification Search
CPC ............ A61M 21/00–02; A61B 5/7264–7267
See application file for complete search history.

(56) References Cited

U.S. PATENT DOCUMENTS

| 11,813,406 B2 | 11/2023 | Dicarlo et al. |
| 2004/0236389 A1 | 11/2004 | Fink et al. |
| 2020/0345968 A1 | 11/2020 | Dicarlo et al. |

FOREIGN PATENT DOCUMENTS

| JP | 2010-257343 A | 11/2010 |
| WO | WO 2019/067783 A1 | 4/2019 |

OTHER PUBLICATIONS

International Search Report and Written Opinion for International Application No. PCT/US2020/030804 mailed Sep. 24, 2020.
(Continued)

*Primary Examiner* — Thaddeus B Cox
(74) *Attorney, Agent, or Firm* — Wolf, Greenfield & Sacks, P.C.

(57) ABSTRACT

Techniques for non-invasively controlling targeted neural activity of a subject are provided herein. The techniques include applying a stimulus input to the subject, the stimulus input being formed by a deep artificial neural network (ANN) model and being configured to elicit targeted neural activity within a brain of the subject. The stimulus input may be a pattern of luminous power generated by the deep ANN model and applied to retinae of the subject. The stimulus input may be generated by the deep ANN model based on a mapping of the subject's neural responses to neurons of the deep ANN model.

20 Claims, 30 Drawing Sheets

(56) References Cited

OTHER PUBLICATIONS

Invitation to Pay Additional Fees for International Application No. PCT/US2020/030804 mailed Jul. 21, 2020.
International Preliminary Report on Patentability mailed Nov. 11, 2021 for International Application No. PCT/US2020/030804.
Cadena et al., Deep convolutional models improve predictions of macaque V1 responses to natural images. PLoS computational biology. Apr. 23, 2019;15(4):e1006897.
Carlson et al., A sparse object coding scheme in area V4. Current Biology. Feb. 22, 2011;21(4):288-93.
Cavanaugh et al., Nature and interaction of signals from the receptive field center and surround in macaque V1 neurons. Journal of neurophysiology. Nov. 1, 2002;88(5):2530-46.
Cheng et al., Comparison of neuronal selectivity for stimulus speed, length, and contrast in the prestriate visual cortical areas V4 and MT of the macaque monkey. Journal of Neurophysiology. Jun. 1, 1994;71(6):2269-80.
Cichy et al., Comparison of deep neural networks to spatio-temporal cortical dynamics of human visual object recognition reveals hierarchical correspondence. Scientific reports. Jun. 10, 2016;6:27755.
Cox et al., Receptive field focus of visual area V4 neurons determines responses to illusory surfaces. Proceedings of the National Academy of Sciences. Oct. 15, 2013;110(42):17095-100.
Deng et al., Imagenet: A large-scale hierarchical image database. 2009 IEEE conference on computer vision and pattern recognition. Jun. 20, 2009:248-255.
Desimone et al., Stimulus-selective properties of inferior temporal neurons in the macaque. Journal of Neuroscience. Aug. 1, 1984;4(8):2051-62.
Erhan et al., Visualizing higher-layer features of a deep network. University of Montreal. Jun. 9, 2009;1341(3):1-13.
Freeman et al., A functional and perceptual signature of the second visual area in primates. Nature neuroscience. Jul. 2013;16(7):974-81.
Goodfellow et al., Explaining and harnessing adversarial examples. ArXiv preprint arXiv:1412.6572v1. Dec. 20, 2014;v1:1-10.
Hinkle et al., Three-dimensional orientation tuning in macaque area V4. Nature neuroscience. Jul. 2002;5(7):665-70.
Hubel et al., Receptive fields and functional architecture of monkey striate cortex. The Journal of physiology. Mar. 1, 1968;195(1):215-43.
Hubel et al., Receptive fields, binocular interaction and functional architecture in the cat's visual cortex. The Journal of physiology. Jan. 1962;160(1):106-54.
Jazayeri et al., Navigating the neural space in search of the neural code. Neuron. Mar. 8, 2017;93(5):1003-14.
Khaligh-Razavi et al., Deep supervised, but not unsupervised, models may explain IT cortical representation. PLoS computational biology. Nov. 6, 2014;10(11):e1003915.
Klindt et al., Neural system identification for large populations separating "what" and "where". Advances in Neural Information Processing Systems. 2017;30:3506-16.
Kobatake et al., Neuronal selectivities to complex object features in the ventral visual pathway of the macaque cerebral cortex. Journal of neurophysiology. Mar. 1, 1994;71(3):856-67.
Kohitij et al., Evidence that recurrent circuits are critical to the ventral stream's execution of core object recognition behavior. BioRxiv. Jun. 24, 2018:1-20.
Kosai et al., The role of visual area V4 in the discrimination of partially occluded shapes. Journal of Neuroscience. Jun. 18, 2014;34(25):8570-84.
Krizhevsky et al., ImageNet Classification with Deep Convolutional Neural Networks. Advances in Neural Information Processing Systems. 2012:1-9.
Kubilius et al., Cornet: Modeling the neural mechanisms of core object recognition. BioRxiv. Sep. 4, 2018:1-9.
Kurakin et al., Adversarial examples in the physical world. ArXiv preprint arXiv:1607.02533v4. Feb. 11, 2017;4:1-14.
Majaj et al., Simple learned weighted sums of inferior temporal neuronal firing rates accurately predict human core object recognition performance. Journal of Neuroscience. Sep. 30, 2015;35(39):13402-18.
Pasupathy et al., Population coding of shape in area V4. Nature neuroscience. Dec. 2002;5(12):1332-8.
Pasupathy et al., Responses to contour features in macaque area V4. Journal of neurophysiology. Nov. 1, 1999;82(5):2490-502.
Pasupathy et al., Shape representation in area V4: position-specific tuning for boundary conformation. Journal of neurophysiology. Nov. 1, 2001;86(5):2505-19.
Pearl, Causality. Cambridge university press. Sep. 14, 2009:485 pages.
Popivanov et al., Heterogeneous single-unit selectivity in an fMRI-defined body-selective patch. Journal of Neuroscience. Jan. 1, 2014;34(1):95-111.
Rajalingham et al., Comparison of object recognition behavior in human and monkey. Journal of Neuroscience. Sep. 2, 2015;35(35):12127-36.
Rajalingham et al., Large-scale, high-resolution comparison of the core visual object recognition behavior of humans, monkeys, and state-of-the-art deep artificial neural networks. Journal of Neuroscience. Aug. 15, 2018;38(33):7255-69.
Schrimpf et al., Brain-score: Which artificial neural network for object recognition is most brain-like?. BioRxiv. Jan. 3, 2020:1-9.
Shen et al., End-to-end deep image reconstruction from human brain activity. Frontiers in computational neuroscience. Apr. 12, 2019;13:21.
Tsao et al., A cortical region consisting entirely of face-selective cells. Science. Feb. 3, 2006;311(5761):670-674.
Watson, A formula for human retinal ganglion cell receptive field density as a function of visual field location. Journal of vision. Jun. 1, 2014;14(7):1-17.
Yamins et al., Hierarchical modular optimization of convolutional networks achieves representations similar to macaque IT and human ventral stream. Advances in neural information processing systems. 2013:1-9.
Yamins et al., Performance-optimized hierarchical models predict neural responses in higher visual cortex. Proceedings of the National Academy of Sciences. Jun. 10, 2014;111(23):8619-24.
Yamins et al., Using goal-driven deep learning models to understand sensory cortex. Nature neuroscience. Mar. 2016;19(3):356-65.
Zeiler et al., Visualizing and understanding convolutional networks. European conference on computer vision. Sep. 6, 2014:818-833.

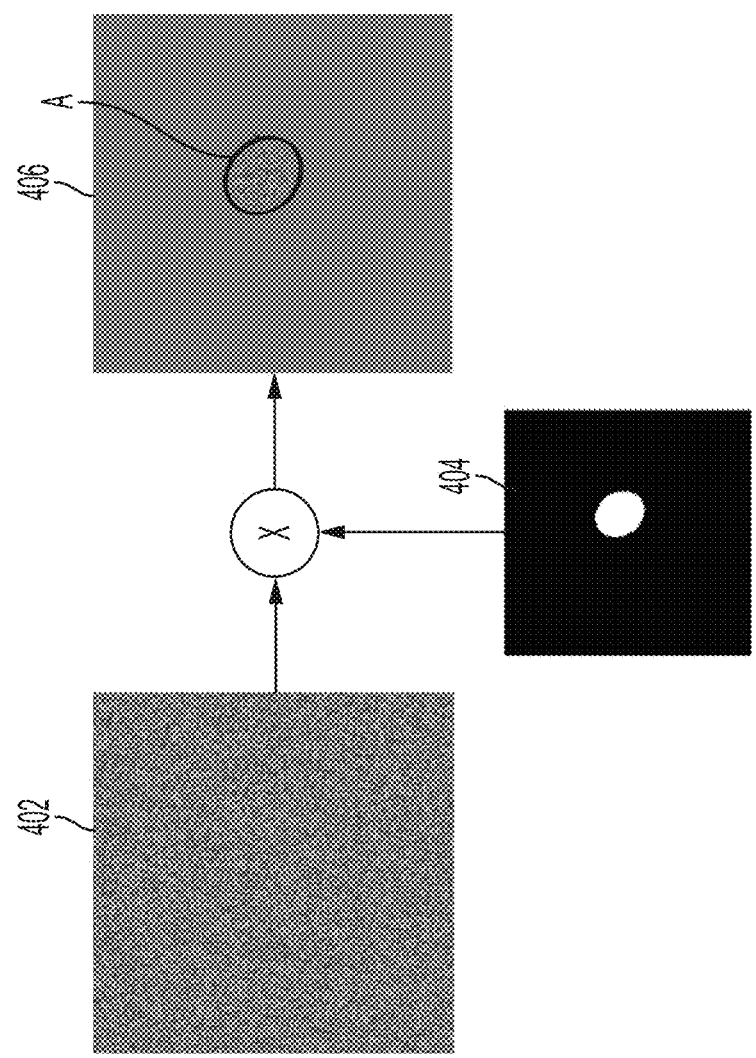

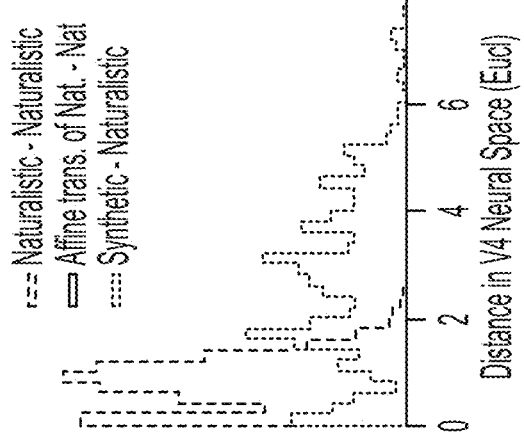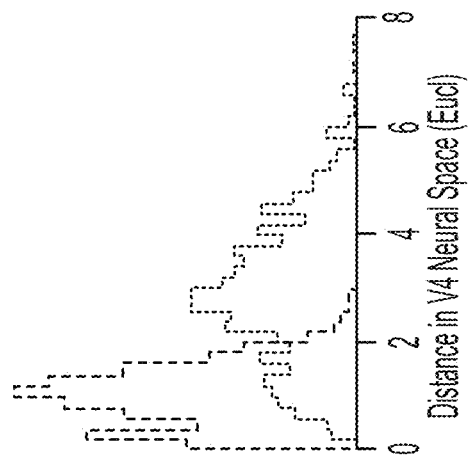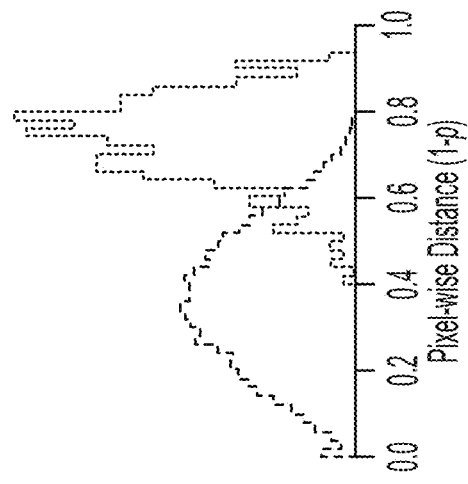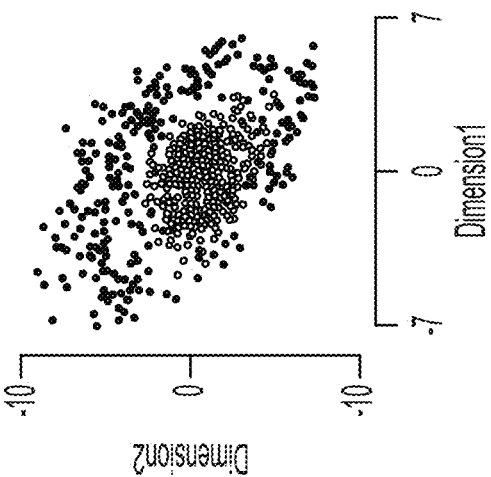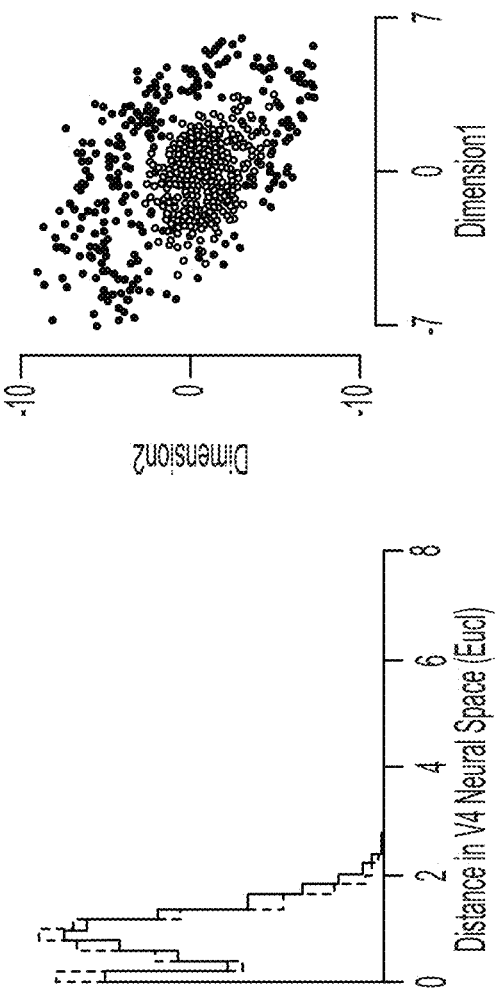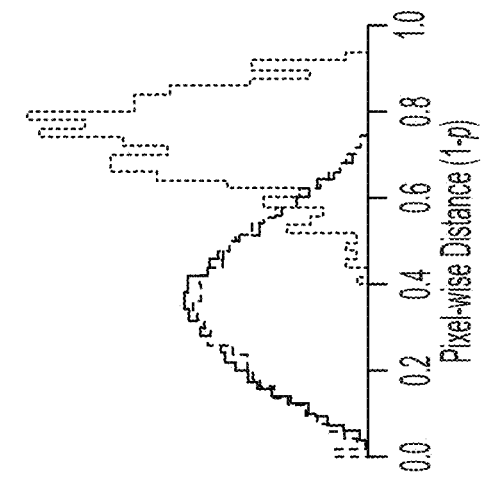
FIG. 15A
FIG. 15B
FIG. 15C
FIG. 15D
FIG. 15E
FIG. 15F

SOFTWARE AND METHODS FOR CONTROLLING NEURAL RESPONSES IN DEEP BRAIN REGIONS

CROSS-REFERENCE TO RELATED APPLICATIONS

The present application claims benefit under 35 U.S.C. § 120 as a Divisional of U.S. patent application Ser. No. 16/863,781, entitled "Software and Methods for Controlling Neural Responses in Deep Brain Regions", filed Apr. 30, 2020, which claims benefit under 35 U.S.C. § 119 (e) of U.S. Provisional Patent Application No. 62/841,445, filed May 1, 2019, and titled "Software and Methods for Controlling Neural Responses in Deep Brain Regions," which is hereby incorporated by reference herein in its entirety. U.S. patent application Ser. No. 16/863,781 has now issued as U.S. Pat. No. 11,813,406.

FEDERALLY SPONSORED RESEARCH

This invention was made with government support under N00014-14-1-0671 awarded by the Office of Naval Research, and EY014970 awarded by the National Institutes of Health. The government has certain rights in the invention.

BACKGROUND

Deep artificial neural network (ANN) models are computing systems that can learn to perform complex tasks without being programmed with task-specific rules. Examples of such complex tasks include image recognition, speech recognition, and machine translation, among many others. Deep ANN models are systems formed from a collection of connected computing nodes, called artificial neurons, that can transmit information to other nodes within the system to perform an assigned task. In this way, deep ANN models can serve as a computer-based analogue to biological brains.

SUMMARY

The following is a non-limiting summary of some embodiments described in the present application.

In one embodiment, there is provided a method of controlling targeted neural activity of a subject. The method comprises applying a stimulus input to the subject. The stimulus input is formed by a deep artificial neural network (ANN) model and is configured to elicit targeted neural activity within a brain of the subject.

In another embodiment, there is provided a system to control neural activity of a subject. The system comprises at least one processor configured to access stimulus input images stored by at least one computer memory, and an apparatus, coupled to the processor, configured to apply the stimulus input images to retinae of the subject. The stimulus input images are formed by a deep ANN model.

In a further embodiment, there is provided a method of controlling targeted neural activity of a subject. The method comprises generating a stimulus input image configured to control targeted neural activity of the subject. The generating comprises mapping neural activity of the subject responsive to one or more naturalistic images of a brain region to a deep ANN model, generating an initial image comprising random pixel values, masking the initial image with a receptive field of a neuron of the brain region of the species to form a masked image, and using the deep ANN model to synthesize the stimulus input image based on the masked image.

The method further comprises applying the generated stimulus input image to retinae of the subject.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 4A is an illustrative example of masking an initial image with a receptive field of a neuron as a part of generating a stimulus image using a deep ANN model, in accordance with some embodiments described herein;

FIGS. 15A-15F show distributions plotting minimum distances of each image in the test set compared to the full set of naturalistic images in Euclidean and pixel-space distances and the relative locations of naturalistic and synthesized stimulus images in measured V4 population response space for a single subject, in accordance with some embodiments described herein;

DETAILED DESCRIPTION

Figure 1:
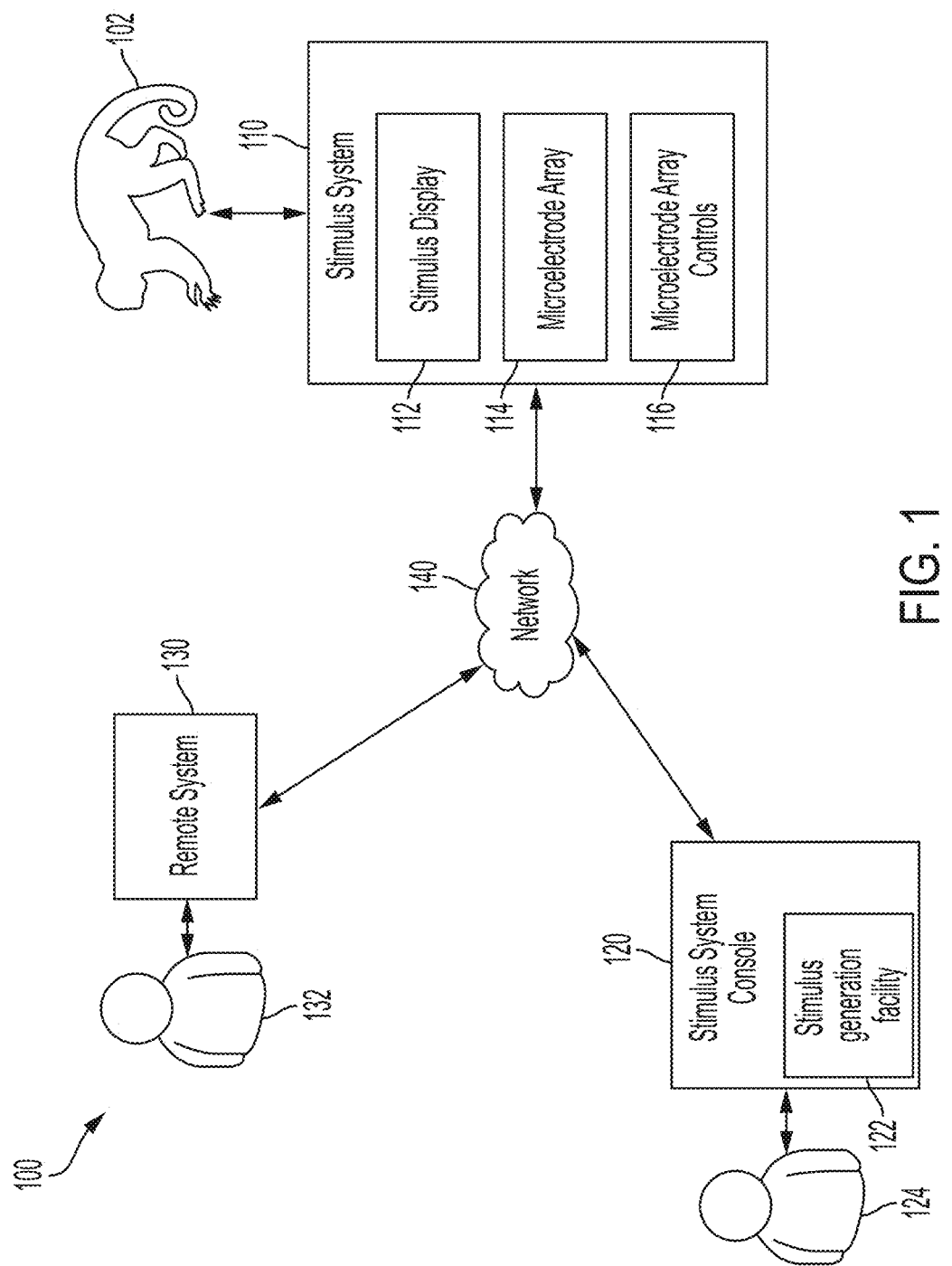
FIG. 1 is a schematic diagram of a facility for performing neural stimulus processes, in accordance with some embodiments described herein.

Described herein are techniques for non-invasively controlling and/or eliciting targeted neural responses using stimulus inputs generated by a deep artificial neural network (ANN) model. These techniques include methods of applying a stimulus input (e.g., a stimulus input image) to a subject (e.g., to the retinae of the subject) and, in some embodiments, measuring resulting neural site responses to the applied stimulus inputs. These techniques further include methods of generating a stimulus input using a deep ANN model by mapping artificial neurons of the deep ANN model to a visual processing area of a subject's brain. In some embodiments described herein, the stimulus input may be configured to increase the firing rate of a single neural site without regulating the activity of other neural sites. In other embodiments, the stimulus input may be configured to control the firing rate of a single neural site and may suppress the activity of other neural sites.

Deep feed-forward artificial neural network (ANN) models can provide an understanding of the approximately 200 ms of initial visual processing in the primate ventral visual stream and the core object recognition behavior it supports. In particular, visually-evoked internal neural representations of some ANNs are remarkably similar to the visually-evoked neural representations in mid-level (area V4) and high-level (area IT) cortical stages of the primate ventral visual stream. This finding has been extended to neural representations in visual area V1, to patterns of behavioral performance in core object recognition tasks, and to both magnetoencephalography and fMRI measurements of the human ventral visual stream.

However, at least two potential limitations of the proposed ANN model-brain similarities have been raised. First, because the visual processing that is executed by such ANN models is not simple to describe, and ANN models have been evaluated only in terms of internal functional similarity to the brain, the ANN models may function more like a copy of, rather than a useful understanding of, the ventral visual stream. The inventors have recognized and appreciated that the detailed knowledge of an ANN model may be assessed by using an ANN model to generate a stimulus configured to perform neural activity control in a non-human primate subject.

Second, because the images in previous studies to assess similarity between ANN models and the brain were sampled from the same distribution as that used to set the ANN model's internal parameters, it is unclear if these ANN models would pass a stronger test of functional similarity based on entirely novel images. The reported apparent functional similarity of the ANN models to the brain may be an overestimation of their true functional similarity. The inventors have further recognized and appreciated that this second limitation may be assessed by determining if the functional similarity of the ANN model and the brain generalizes to entirely novel images.

Accordingly, the inventors have developed systems and methods for performing targeted neural control using stimulus inputs generated by a deep ANN model. Particularly, the inventors used a deep ANN ventral stream model (e.g., a specific ANN model with a fully fixed set of parameters) to synthesize new patterns of luminous power ("controller images") that, when applied to the retinae of a subject, where intended to control the neural firing activity of particular, experimenter-chosen and targeted neural sites in cortical visual area V4 of macaque subjects. Further, the inventors have developed systems to synthesize two types of stimulus input images to perform two functions: (1) neural "stretch" images that stretch (e.g., increase) a firing rate of a single targeted neural site beyond a naturally occurring maximal neural firing rate, and (2) neural population state control images that independently control neural sites in a small recorded population (here, populations of 5-40 neural sites). The neural population state control images described herein are configured to drive the V4 population into an experimenter-chosen "one hot" state in which one neural site is pushed to be highly active while all other nearby sites are simultaneously "clamped" at their baseline activation level. Such non-invasive control of the brain using an ANN model provides a practical test of useful, causal "understanding" of the ANN model of the brain.

In some embodiments, the method of non-invasively controlling targeted neural activity of a subject may include applying a stimulus input to the subject (e.g., a non-human primate, a human). The stimulus input (e.g., a pattern of luminous intensity, an image) may be formed by a deep ANN model and may be configured to elicit targeted neural activity within a brain of the subject. In some embodiments, the stimulus input may be configured to increase the firing rate of a single neural site, without regulating the activity of other neural sites. In other embodiments, the stimulus input may be configured to control the firing rate of a single neural site and suppressing the activity of other neural sites.

In some embodiments, the method may include generating the stimulus input using a deep ANN model. The stimulus input may be generated by mapping neural activity of a brain region of a subject responsive to one or more naturalistic images to the deep ANN model. For example, one or more artificial neurons of the deep ANN model may be mapped to each recorded V4 neural site using a mapping function (e.g., an image-computable predictive model of the activity of each recorded V4 neural site). The stimulus input may then be generated by the deep ANN model based on a generated initial image comprising randomized pixel values. In some embodiments, the initial image may be masked with a receptive field of a neuron or neural site of the subject to form a masked image, and the deep ANN model may then synthesize the stimulus input based on the masked image. For example, the deep ANN model may synthesize the stimulus input by varying pixel values within the masked image in order to minimize one or more loss functions. The synthesized stimulus input may then be applied to the retinae of the subject (e.g., by showing the stimulus input to the subject on a suitable screen or display) to elicit a targeted neural response.

In some embodiments, one or more portions of the above method may be performed by a system configured to non-invasively control neural activity of the subject. The system may include at least one processor configured to access stimulus inputs generated by a deep ANN model and/or to generate the stimulus inputs using a deep ANN model. For example, the at least one processor may access the stimulus inputs from at least one computer memory. Additionally, the system may include an apparatus configured to apply the stimulus input to the subject (e.g., to apply the stimulus input to the retinae of the subject by displaying the stimulus input on a suitable screen or display). In some embodiments, the system may include a device configured to measure a neural response of the subject to the applied stimulus input. For example, the system may include a microelectronic array (e.g., an implanted microelectronic array or an in vitro microelectronic array) configured to measure neural firing rates in the subject.

Following below are more detailed descriptions of various concepts related to, and embodiments of, techniques for non-invasive control of neural activity. It should be appreciated that various aspects described herein may be implemented in any of numerous ways. Examples of specific implementations are provided herein for illustrative purposes only. In addition, the various aspects described in the embodiments below may be used alone or in any combinations and are not limited to the combinations explicitly described herein.

FIG. 1 is a schematic diagram of an example of a facility 100 for performing targeted neural stimulus processes, in accordance with some embodiments described herein. In the illustrative example of FIG. 1, facility 100 includes a stimulus system 110, a stimulus system console 120, and a remote system 130. It should be appreciated that facility 100 is illustrative and that a stimulus facility may have one or more other components of any suitable type in addition to or instead of the components illustrated in FIG. 1. For example, there may be additional remote systems (e.g., two or more) present within a facility.

As illustrated in FIG. 1, in some embodiments, one or more of the stimulus system 110, the stimulus system console 120, and the remote system 130 may be communicatively connected to each other by a network 140. The network 140 may be or include one or more local- and/or wide-area, wired and/or wireless networks, including a local-area or wide-area enterprise network and/or the Internet. Accordingly, the network 140 may be, for example, a hard-wired network (e.g., a local area network within a facility), a wireless network (e.g., connected over Wi-Fi and/or cellular networks), a cloud-based computing network, or any combination thereof. For example, in some embodiments, the stimulus system 110 and the stimulus system console 120 may be located within a same location and connected directly to each other or connected to each other via the network 140, while the remote system 130 may be located at a remote location and connected to the stimulus system 110 and/or the stimulus system console 120 through the network 140.

In some embodiments, the stimulus system 110 may be configured to perform targeted neural stimulus processes of a subject 102. While FIG. 1 illustrates the subject as a non-human primate (e.g., a monkey), other embodiments are not so limited. Some embodiments may operate with other species such as humans or apes. For example, the stimulus system 110 may include a stimulus display 112, a microelectrode array 114, and microelectrode array controls 116 configured to act in concert to perform said targeted neural stimulus processes.

In some embodiments, stimulus display 112 may be configured to display one or more stimulus inputs to the subject 102 during a targeted neural stimulus process. The stimulus display 112 may be any suitable type of display that is configured to display a stimulus input such as a generated pattern of luminous intensity. For example, the stimulus display 112 may include a liquid crystal display (LCD), a light-emitting diode (LED) display, a cathode ray tube (CRT) display, a plasma display panel (PDP), or any other suitable display mechanism.

In some embodiments, microelectrode array 114 may be arranged to measure one or more neural responses within a region of the brain of the subject 102. For example, microelectrode array 114 may be any suitable array including Michigan and/or Utah arrays which may be implanted into the brain of the subject 102. The microelectrode array 114 may be implanted within a specific region of the brain of the subject 102 in order to enable the stimulus system 110 to record specific neural responses of the subject 102 to stimulus input. For example, the microelectrode array 114 may be implanted into a visual area of the brain of the subject 102 (e.g., area V4). In some embodiments, the microelectrode array may be less invasively placed to record activity of the brain of the subject 102 (e.g., the microelectrode array may be electrodes attached to the skull externally).

In some embodiments, microelectrode array controls 116 may be used to record measured neural responses within the brain of the subject 102. For example, microelectrode array controls 116 may be used to record measurements made by one or more electrodes of the microelectrode array 114. Alternatively, microelectrode array controls 116 may transmit measurements made by one or more electrodes of the microelectrode array 114 to another computing system (e.g., stimulus system console 120 and/or remote system 130).

As illustrated in FIG. 1, facility 100 includes stimulus system console 120 communicatively coupled to the stimulus system 110. Stimulus system console 120 may be any suitable electronic device configured to send instructions and/or information to stimulus system 110, to receive information from stimulus system 110, and/or to process obtained neural response data. In some embodiments, stimulus system console 120 may be a fixed electronic device such as a desktop computer, a rack-mounted computer, or any other suitable fixed electronic device. Alternatively, stimulus system console 120 may be a portable device such as a laptop computer, a smart phone, a tablet computer, or any other portable device that may be configured to send instructions and/or information to stimulus system 110, to receive information from stimulus system 110, and/or to process obtained neural response data.

Some embodiments of facility 100 may include a stimulus generation facility 122 within stimulus system console 120. Stimulus generation facility 122 may be configured to generate one or more stimulus inputs using a deep ANN model. Stimulus generation facility 122 may be configured to, for example, analyze neural response data produced by a subject 102 in response to naturalistic images and perform a mapping of the deep ANN model to neural sites within the subject 102 based on the neural response data. Stimulus generation facility 122 may be further configured to, for example, synthesize stimulus inputs to target specific neural sites of the subject using the mapped deep ANN model. For example, stimulus generation facility 122 may be configured to generate an initial image comprising random pixel values, to mask the initial image based on the receptive field of the targeted neural sites, and to generate a stimulus input using the masked initial image and the mapped deep ANN model (e.g., by minimizing one or more loss functions within the mapped deep ANN model).

Stimulus generation facility 122 may be implemented as hardware, software, or any suitable combination of hardware and software, as aspects of the disclosure provided herein are not limited in this respect. As illustrated in FIG. 1, the stimulus generation facility 122 may be implemented in the stimulus system console 120, such as by being implemented in software (e.g., executable instructions) executed by one or more processors of the stimulus system console 120. However, in other embodiments, the stimulus generation facility 122 may be additionally or alternatively implemented at one or more other elements of the system 100 of FIG. 1. For example, the stimulus generation facility 122 may be implemented at the stimulus system 110 and/or the remote system 130 discussed below. In other embodiments, the stimulus generation facility 122 may be implemented at or with another device, such as a device located remote from the system 100 and receiving data via the network 140.

Stimulus system console 120 may be accessed by user 124 in order to control stimulus system 120 and/or to process neural stimulus data obtained by stimulus system 110. For example, user 124 may implement a neural stimulus process by inputting one or more instructions into stimulus system console 120 (e.g., user 124 may select a desired targeted neural site and/or neural stimulus type from among several options presented by stimulus system console 120). Alternatively or additionally, in some embodiments, user 124 may implement a stimulus input generation procedure by inputting one or more instructions into stimulus system console 120 (e.g., user 124 may select a type of stimulus input to be generated from among several options presented by stimulus system console 120).

As illustrated in FIG. 1, stimulus system console 120 also interacts with remote system 130 through network 140, in some embodiments. Remote system 130 may be any suitable electronic device configured to receive information (e.g., from stimulus system 110 and/or stimulus system console 120) and to display neural response data and/or generated stimulus inputs. The remote system 130 may be remote from the stimulus system 110 and stimulus system console 120, such as by being located in a different room, wing, or building of a facility than the stimulus system 110, or being geographically remote from the stimulus system 110 and stimulus system console 120, such as being located in another part of a city, another city, another state or country, etc. In some embodiments, remote system 130 may be a fixed electronic device such as a desktop computer, a rack-mounted computer, or any other suitable fixed electronic device. Alternatively, remote system 130 may be a portable device such as a laptop computer, a smart phone, a tablet computer, or any other portable device that may be configured to receive and view generated stimulus inputs and/or to send instructions and/or information to stimulus system console 120.

In some embodiments, remote system 130 may receive information (e.g., neural response data, generated stimulus inputs) from stimulus system console 120 and/or stimulus system 110 over the network 140. A remote user 132 may use remote system 130 to view the received information on remote system 130. For example, the remote user 132 may view generated stimulus inputs using remote system 130 after the user 124 has completed stimulus input generation using stimulus system 110 and/or stimulus system console 120.

Figure 2:
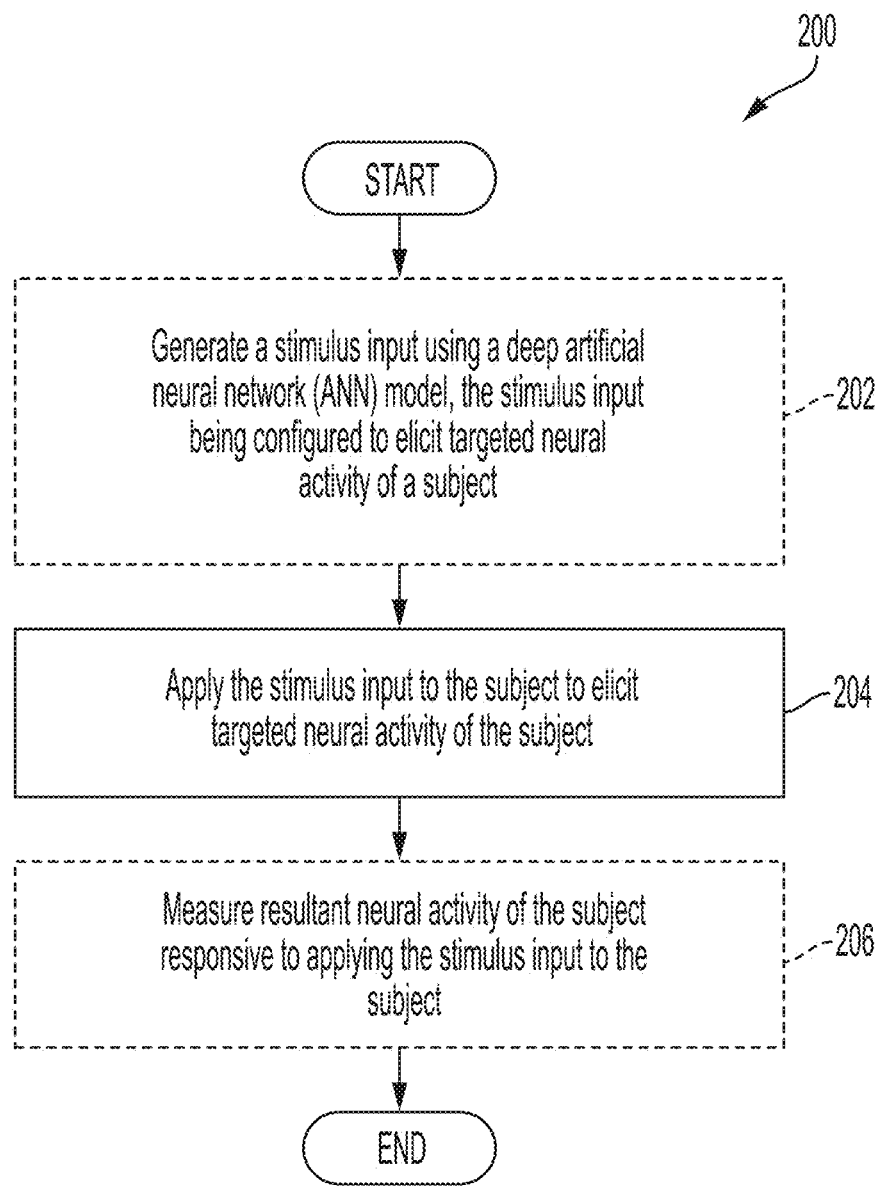
FIG. 2 is a flowchart of an illustrative process 200 of applying a stimulus generated by a deep artificial neural network (ANN) model to a subject, in accordance with some embodiments described herein.

FIG. 2 is a flowchart of an illustrative process 200 of applying a stimulus generated by a deep ANN model to a subject, in accordance with some embodiments described herein. Process 200 may be implemented by a stimulus system, such as the stimulus system 110 of FIG. 1, and/or a stimulus generation facility, such as stimulus generation facility 122 of FIG. 1. As such, in some embodiments, the process 200 may be performed by a computing device configured to send instructions to a stimulus system and/or to receive information from a stimulus system (e.g., stimulus system console 120 executing stimulus generation facility 122 as described in connection with FIG. 1). As another example, in some embodiments, the process 200 may be performed by one or more processors located remotely (e.g., as part of a cloud computing environment, as connected through a network) from the stimulus system that obtained the neural stimulus data from the subject 102.

Process 200 may begin optionally at act 202, where the stimulus generation facility may generate a stimulus input using a deep ANN model. In some embodiments, the stimulus input may be configured to elicit targeted neural activity in a subject (e.g., a non-human primate, a human, another mammal). For example, the stimulus input may be configured to stretch (e.g., increase) a neural firing rate of a targeted neural site or may be configured to control a neural firing rate of a targeted neural site while controlling and/or suppressing a neural firing rate of other measured neural sites. The stimulus input may be generated, for example, by a deep ANN model that is mapped to the subject's neural site responses to naturalistic (e.g., control) stimulus inputs. In some embodiments, the stimulus input may be an image generated using such a deep ANN model configured to alter an initial input image comprising random pixel values by altering the initial image in order to minimize one or more loss functions associated with the targeted neural site and/or specified neural stimulus type (e.g., stretch or population control).

At act 204, the stimulus system may apply the stimulus input (e.g., the stimulus input generated by the stimulus generation facility) to the subject to elicit targeted neural activity. For example, the stimulus system may display a stimulus input image to the subject using a stimulus display (e.g., stimulus display 112 as described in connection with FIG. 1). In some embodiments, the stimulus system may apply the stimulus input to the subject after receiving information about the subject's gaze and/or focus (e.g., by tracking the subject's eye movements).

At act 206, the stimulus system may optionally measure neural activity of the subject in response to the applied stimulus input. In some embodiments, the neural activity may be measured using a microelectrode array (e.g., microelectrode array 114 as described in connection with FIG. 1). The microelectrode array may be implanted into the brain of the subject to measure neural responses of one or more neurons within a neural region. In some embodiments, the microelectrode array may be non-invasively attached to the subject (e.g., electrodes applied to the skull).

Figure 3A:
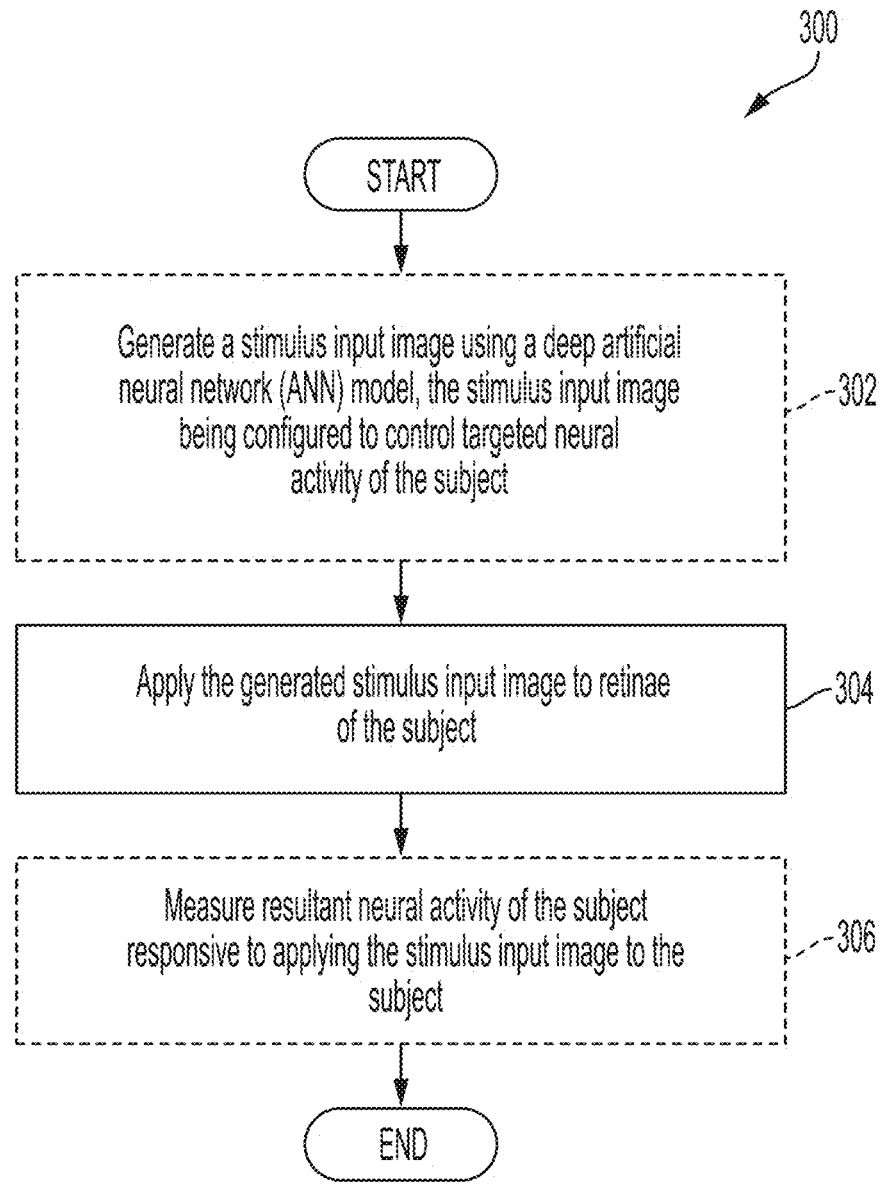
FIG. 3A is a flowchart of an illustrative process 300 of applying a stimulus image generated by a deep ANN model to a subject, in accordance with some embodiments described herein.

FIG. 3A is a flowchart of an illustrative process 300 of generating and applying a stimulus image generated by a deep ANN model to a subject, in accordance with some embodiments described herein. Process 300 may be implemented by a stimulus system, such as the stimulus system 110 of FIG. 1, and/or a stimulus generation facility, such as stimulus generation facility 122 of FIG. 1. As such, in some embodiments, the process 300 may be performed by a computing device configured to send instructions to a stimulus system and/or to receive information from a stimulus system (e.g., stimulus system console 120 executing stimulus generation facility 122 as described in connection with FIG. 1). As another example, in some embodiments, the process 300 may be performed by one or more processors located remotely (e.g., as part of a cloud computing environment, as connected through a network) from the stimulus system that obtained the neural stimulus data from the subject 102.

Process 300 may begin at act 302, where the stimulus generation facility may generate a stimulus input image using a deep ANN model. In some embodiments, the stimulus input may be configured to control or elicit targeted neural activity of a subject (e.g., a non-human primate, a human, another mammal). For example, the stimulus input may be configured to stretch (e.g., increase) a neural firing rate of a targeted neural site or may be configured to control a neural firing rate of a targeted neural site while controlling and/or suppressing a neural firing rate of other measured neural sites.

Figure 3B:
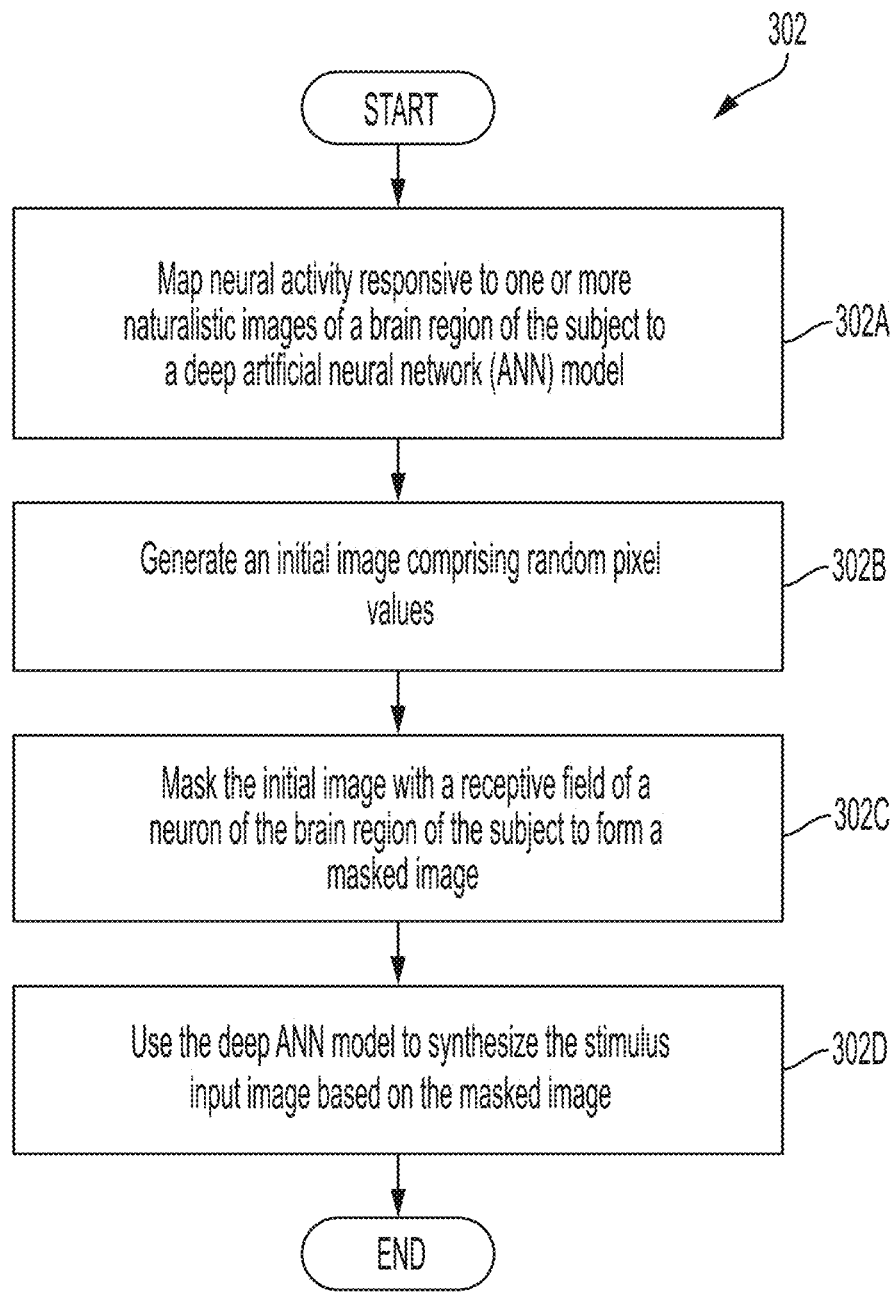
FIG. 3B is a flowchart of an illustrative act 302 of generating a stimulus image using a deep ANN model, in accordance with some embodiments described herein.

Act 302 is described in further detail with reference to FIG. 3B, which is a flowchart of an illustrative process for generating a stimulus image using a deep ANN model, in accordance with some embodiments described herein. Act 302 may begin with act 302A, where neural activity of the subject may be mapped to the deep ANN model. For example, the activity of the subject's neural sites in response to naturalistic images (e.g., control images) may be mapped to artificial neurons of the deep ANN model. The neural activity of the subject may be mapped to the deep ANN model using a mapping function (e.g., a linear mapping function) so that the deep ANN model may provide an accurate model of the neural responses of the subject.

Act 302 may then proceed to act 302B, in which the stimulus generation facility may generate an initial image. The initial image may comprise random pixel values (e.g., as generated by a random number generator or other suitable randomness generator). The initial image may then be masked in act 302C with a receptive field of a neuron or neural site of the brain of the subject to form a masked image comprising random pixel values within the region representing the receptive field.

Act 302 may then proceed to act 302D, where the deep ANN model may synthesize the stimulus input image based on the masked image. For example, the deep ANN model may alter the random pixel values of the masked image in order to minimize one or more loss functions associated with the particular neural site of interest and/or the neural stimulus type (e.g., stretch or population control). In this way, the masked image may be transformed by the deep ANN model into the synthesized stimulus input image configured to elicit a targeted neural response.

Returning to FIG. 3A, in act 304, the generated stimulus input image may be applied to retinae of the subject. For example, the stimulus system may display a stimulus input image to the subject using a stimulus display (e.g., stimulus display 112 as described in connection with FIG. 1). In some embodiments, the stimulus system may apply the stimulus input to the subject after receiving information about the subject's gaze and/or focus (e.g., by tracking the subject's eye movements).

At act 306, the stimulus system may optionally measure neural activity of the subject in response to the applied stimulus input. In some embodiments, the neural activity may be measured using a microelectrode array (e.g., microelectrode array 114 as described in connection with FIG. 1). The microelectrode array may be implanted into the brain of the subject to measure neural responses of one or more neurons within a neural region.

FIG. 4A is an illustrative example of masking an initial image with a receptive field of a neural site as a part of generating a stimulus input image using a deep ANN model, in accordance with some embodiments described herein. The stimulus generation facility may generate initial image 402 as a part of a process of generating a stimulus input image (e.g., as described in act 302 of process 300). Initial image 402 may comprise random pixel values. The stimulus generation facility may generate and/or access a mask 404 comprising a mask of the receptive field of the neural site to be targeted by the final synthesized stimulus input image. The stimulus generation facility may apply mask 404 to form masked image 406, in which the pixel values of the initial image 402 are visible within the receptive field A. The stimulus generation facility may then generate the stimulus input image by altering the pixels within the receptive field A of masked image 406.

Figure 4B:
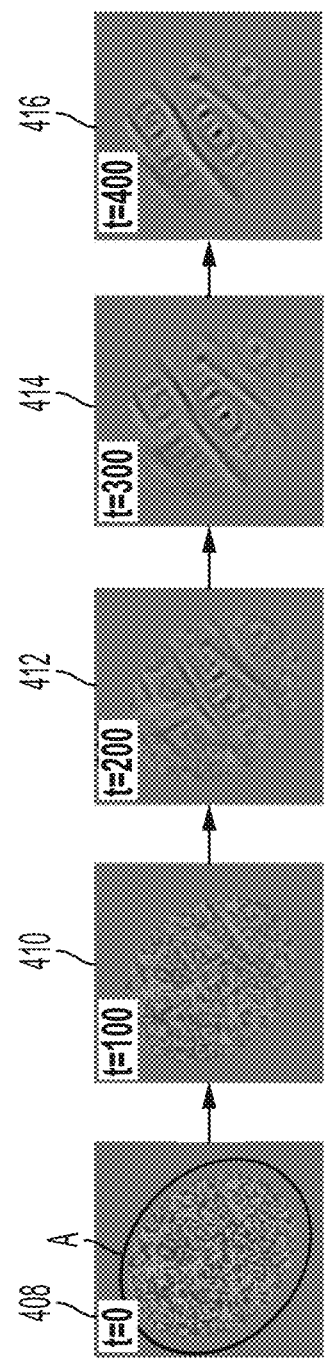
FIG. 4B is an illustrative example of generating a stimulus image using a deep ANN model based on a masked initial image, in accordance with some embodiments described herein.

FIG. 4B is an illustrative example of time steps of a process of generating a stimulus image using a deep ANN model based on a masked initial image, in accordance with some embodiments described herein. Initially, the receptive field A may comprise random pixel values as shown in image 408. The deep ANN model may alter the pixel values within the receptive field A (e.g., of masked image 406 as described in connection with FIG. 4A) to minimize one or more loss functions associated with the targeted neural site(s). The deep ANN model may iteratively alter the pixel values within the receptive field A. An example of this iterative process is shown in images 410, 412, 414, and 416, which represent subsequent time steps within the image generation process, yielding resultant stimulus input image 416.

Following below are more detailed descriptions of implementations of techniques for non-invasive control of neural activity in rhesus macaque subjects. Chronic, implanted microelectrode arrays were used to record the responses of 107 neural multi-unit and single-unit sites from visual area V4 in three awake, fixating rhesus macaques (monkey M, monkey N, and monkey S; $n_M=52$, $n_N=33$, $n_S=22$). The classical receptive field (cRF) of each neural site for each subject was first determined with briefly presented small squares, and each neural site was then tested using a set of 640 naturalistic images. The naturalistic images were always presented to cover the central 8° of the visual field that overlapped with the estimated cRFs of all the recorded V4 sites. Additionally, each neural site was tested using a set of 370 complex curvature stimuli previously determined to be good drivers of V4 neurons, the locations of the complex curvature stimuli being tuned for the cRFs of the neural sites. Using each site's visually evoked responses to 90% of the naturalistic images (n=576), a mapping from a single "V4" layer of a deep ANN model (e.g., the Conv-3 layer) to the neural site responses was created. The Conv-3 layer was selected because it maximally predicted the area V4 responses to the set of naturalistic images using a linear mapping function and was consistent with a similarity analysis performed using a representational dissimilarity matrix. The predictive accuracy of this model-to-brain mapping has previously been used as a measure of the functional fidelity of the brain model to the brain, and using the V4 responses to the held-out 10% of the naturalistic images as tests, it was found that the neural predictor models correctly predicted 89% of the explainable (e.g., image-driven) variance in the V4 neural responses (median over the 107 sites, each site computed as the mean over two mapping/testing splits of the data).

Besides generating a model-V4-to-brain-V4 similarity score (89%, above), this mapping procedure produces an image-computable predictor model of the visually-evoked firing rate of each of the V4 neural sites. If truly accurate, this predictor model is not simply a data fitting device and not just a similarity scoring method-instead it may implicitly capture a great deal of visual "knowledge" that may be difficult to express in human language, but may be hypothesized by the model to be used by the subject's brain to achieve successful visual behavior. To extract and deploy that knowledge, a model-driven image synthesis algorithm may be used, as described herein and in connection with FIGS. 5A through 5E, to generate controller images that may be customized for each neural site (e.g., according to its predictor model) so that each image should predictably and reproducibly control the firing rates of V4 neurons in a particular, experimenter-chosen way. This method may allow for a test of the hypothesis that an experimenter-delivered application of a particular pattern of luminous power on the subject's retinae may reliably and reproducibly cause V4 neurons to move to a particular, experimenter-specified activity state and that removal of that pattern of luminous power will return those V4 neurons to their background firing rates.

Figure 5A:
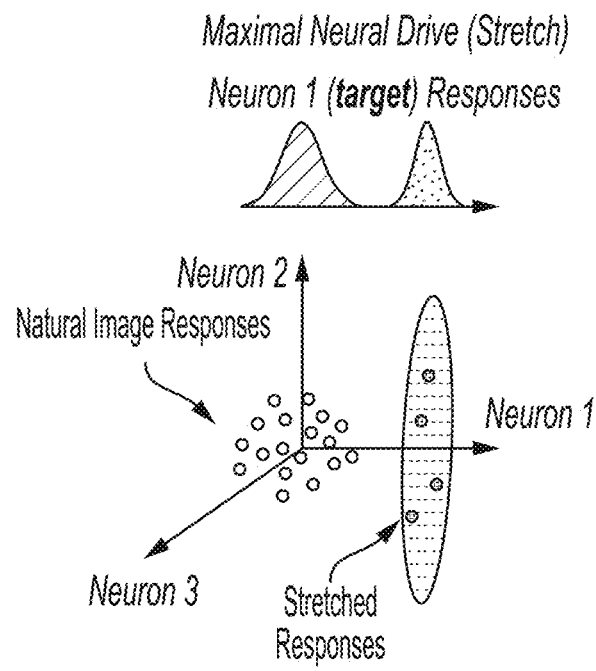
FIG. 5A is a schematic illustration of a neural response to a stimulus image configured to drive the firing rate of a target neural site without regulating activity of other measured neural sites, in accordance with some embodiments described herein.
Figure 5B:
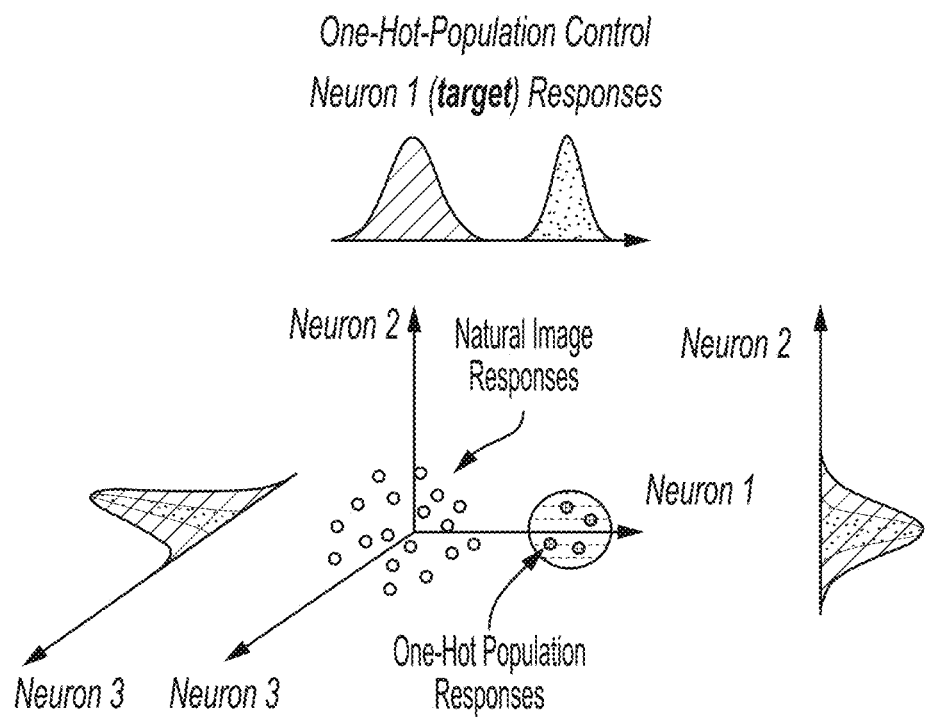
FIG. 5B is a schematic illustration of a neural response to a stimulus image configured to drive the firing rate of a target neural site and suppress activity of other measured neural sites, in accordance with some embodiments described herein.

FIG. 5A is a schematic illustration of a neural response to a synthesized stimulus input image configured to drive the firing rate of a target neural site in a stretch control mode, in accordance with some embodiments described herein. In this case, the algorithm used to generate the stimulus input image is not configured to attempt to regulate the neural activity of other measured neurons (e.g., they might also increase as shown in FIG. 5A). In contrast, FIG. 5B is a schematic illustration of a neural response to a stimulus input image configured to drive the firing rate of a target neural site and suppress activity of other measured neural sites in a one-hot population control mode, in accordance with some embodiments described herein.

Figure 5C:
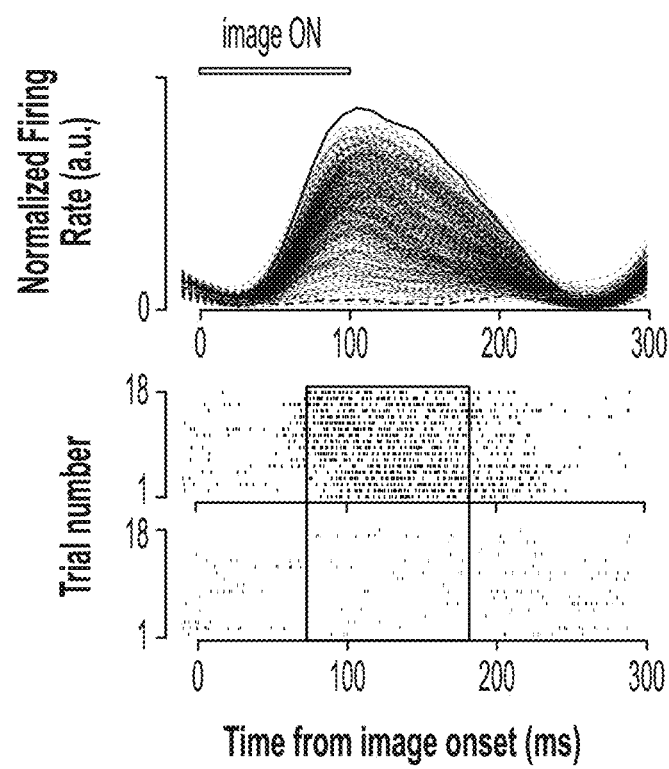
FIG. 5C is an illustrative example of responses of a single V4 neural site to 640 naturalistic images, in accordance with some embodiments described herein.

FIG. 5C is an illustrative example of responses of a single V4 neural site to 640 naturalistic images, in accordance with some embodiments described herein. The responses shown were averaged over approximately 40 repetitions for each image. The wide black line at the top left of the plot marks the image presentation period (e.g., Image ON). The bottom raster plot shows the highest (top) and lowest (bottom) neural response to naturalistic images. The area encompassed by a box in the bottom raster plot indicates the time window over which the activity level of each V4 neural site was computed (e.g., one value per image for each neural site).

Figure 5E:
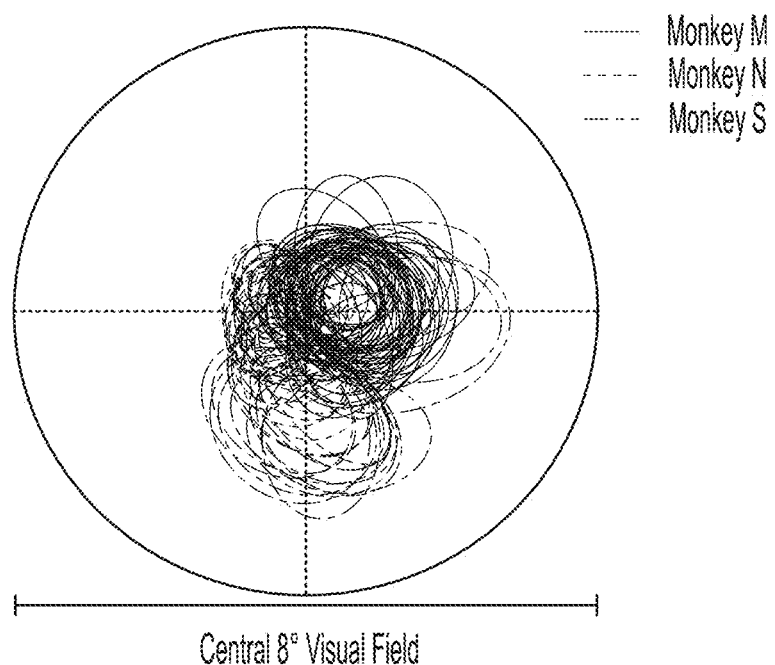
FIG. 5E is an illustrative example of classical receptive fields of neural sites for three monkey subjects, in accordance with some embodiments described herein.
Figure 5D:
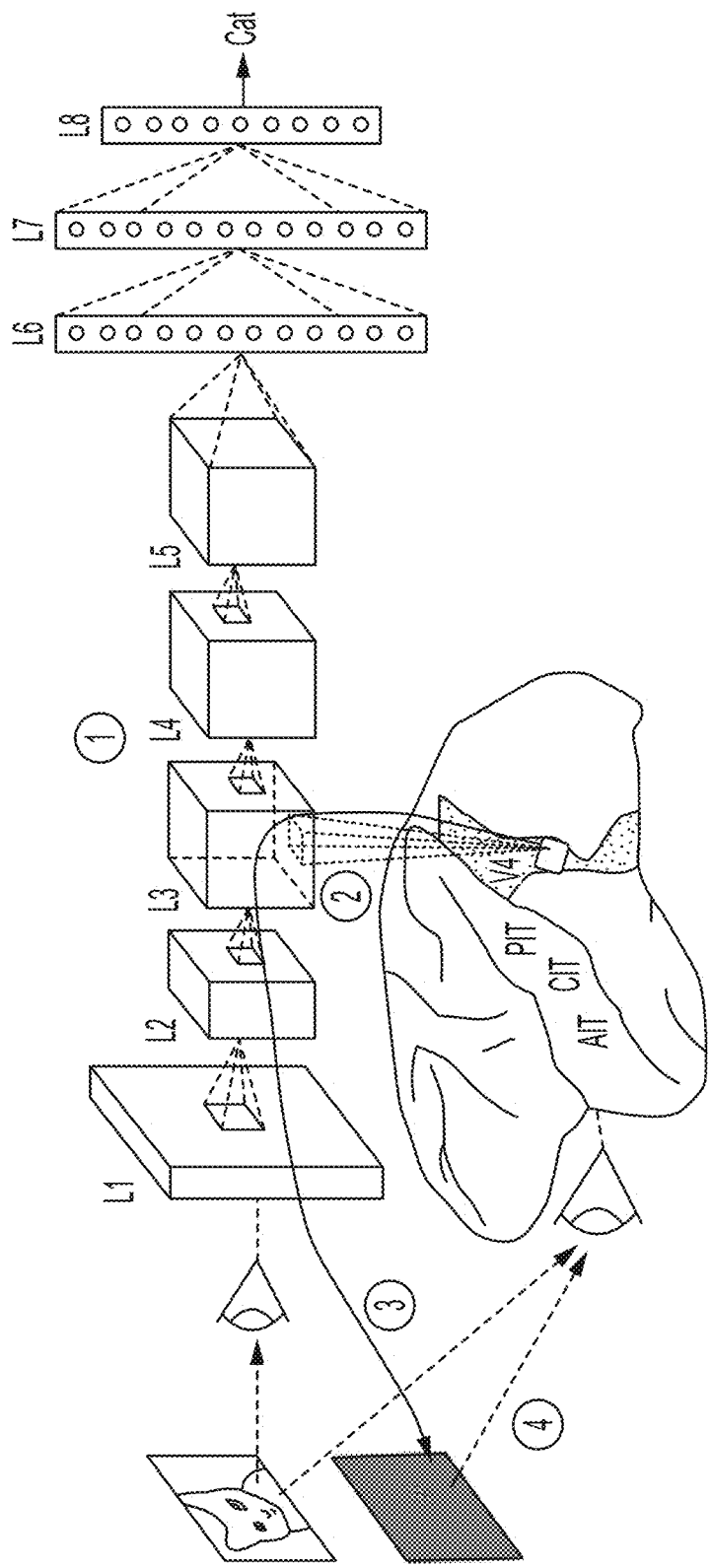
FIG. 5D is an schematic illustration of a neural control experiment, in accordance with some embodiments described herein.

FIG. 5D is a schematic illustration of a neural control experiment, in accordance with some embodiments described herein. The neural control experiments may be performed in four acts. In act (1), parameters of the neural network may be optimized by training on a large set of labeled natural images (ImageNet) and then held constant thereafter. In act (2) "neurons" of the deep ANN model may be mapped to each recorded V4 neural site, as described herein. The mapping function may constitute an image-computable predictive model of the activity of each of those V4 sites. In act (3), the resulting differentiable model may then be used to synthesize "controller" images (e.g., stimulus input images) for either single-site or population control. In act (4), the luminous power patterns of the generated stimulus input images bay be applied to the subject's retinae, and the degree of control of the neural sites may be measured (e.g., by using a microelectrode array).

FIG. 5E shows classical receptive fields (cRFs) of neural sites for the three monkey subjects used herein. The cRFs shown are for each measured neural site of monkey M, Monkey N, and Monkey S. To estimate the cRF of each neural site, approximately 1°×1° white squares were flashed across the central 8° of the monkeys' visual field. The corresponding neural responses were measured and a 2D Gaussian fitted to the data. The cRFs were defined as 1 standard deviation of each neural site.

As described herein, targeted neural control was restricted to the V4 spiking activity that may occur 70-170 ms after retinal power input, which represents the time frame where the ANN models are presumed to be most accurate. Two control settings are described herein: Stretch control and One-hot population control. To test and quantify the goodness of these control settings, patterns of luminous power specified by the synthesized controller images were applied to the retinae of the animal subjects while the responses of the same V4 neural sites were recorded.

Each application of a pattern of luminous power on the retinae are referred to herein as "presentation of an image," but it may be appreciated that the precise manipulation described herein of applied power that is under experimenter control and fully randomized with other applied luminous power patterns (other images) to emphasize that this is logically identical to more direct energy application (e.g. optogenetic experiments) in that the goodness of experimental control is inferred from the correlation between power manipulation and the neural response in the same way in both cases. The only difference of the two approaches is the assumed mechanisms that intervene between the experimentally-controlled power and the controlled dependent variable (here V4 spiking rate) which are steps that the ANN model aims to approximate with stacked synaptic sums, threshold non-linearities, and normalization circuits. In both the control case presented here and the optogenetics control case, those intervening steps are not fully known, but approximated by a model of some type. That is, neither experiment is "only correlational" because causality is inferred from experimenter-delivered, experimenter-randomized application of power to the system.

Because each experiment was performed over separate days of recording (one day to build all the predictor models, one day to test control), only neural sites that maintained both a high signal-to-noise ratio (SNR) and consistent rank order of responses to a standard set of 25 naturalistic images across the two experimental days were considered further ($n_M=38$, $n_N=19$, and $n_S=19$ for Stretch experiments; $n_M=38$, and $n_S=19$ for One-hot-population experiments).

I. "Stretch" Control: Maximizing the Activity of Individual V4 Neural Sites

Each V4 neural site's "naturally-observed maximal firing rate" was first defined as that which was found by testing its response to the best of the 640 naturalistic test images and cross-validated over repeated presentations. Synthetic controller images were then generated for which the synthesis algorithm was instructed to drive a targeted neural site's firing rate as high as possible beyond that rate, regardless of the activity of other V4 neural sites. For the first Stretch Control experiment, the synthesis algorithm was restricted to operate on parts of the image that were within the classical receptive field (cRF) of each neural site (e.g., as described in connection with FIGS. 3 and 4). For each target neural site ($n_M=21$, $n_N=19$, and $n_S=19$), the synthesis algorithm was run for five different random image initializations. For 79% of neural sites, the synthesis algorithm successfully found at least one image that it predicted to be at least 10% above the site's naturally observed maximal firing rate.

Figure 10:
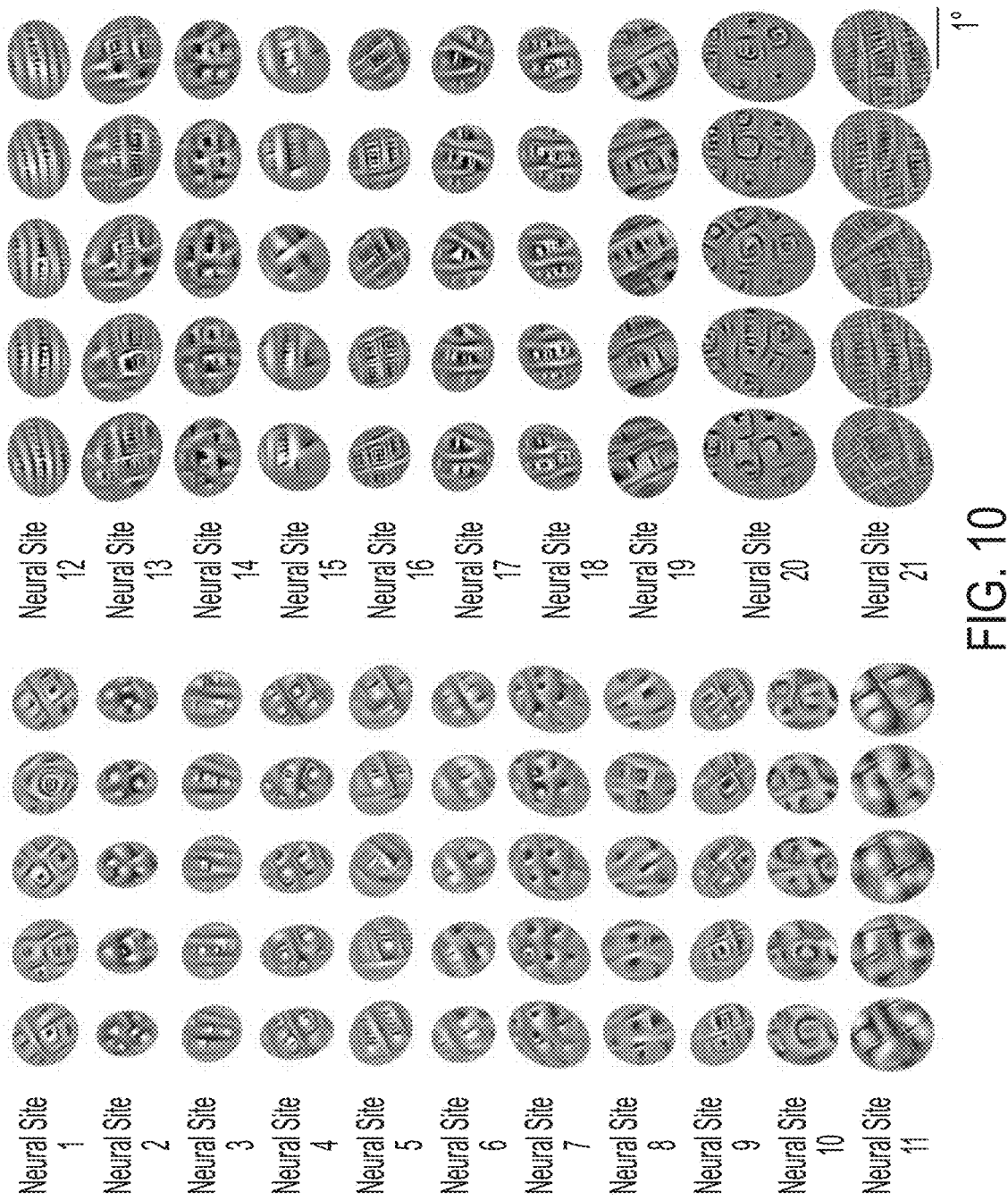
FIG. 10 shows examples of stimulus images configured to drive the firing rate of a target neural site without regulating activity of other measured neural sites for 21 neural sites in a subject, in accordance with some embodiments described herein.

However, in the interest of presenting an unbiased estimate of the stretch control goodness for randomly sampled V4 neural sites, all sites were included in the analyses, even those (~20%) that the control algorithm predicted that it could not "stretch." Visual inspection suggests that the five stretch controller images generated by the algorithm for each neural site are perceptually more similar to each other compared to those generated for different neural sites, but that similarity was not psychophysically quantified. FIG. 10 shows examples of synthesized controller images configured to perform stretch control and drive the firing rate of a target neural site without regulating activity of other measured neural sites for 21 example V4 neural sites in monkey M, in accordance with some embodiments described herein. Each column displays images generated using the same random starting image, but optimized for each target neural site. Note the perceptual similarity of the controller images synthesized for each site and the dissimilarity between the controller images across sites.

Figure 6A:
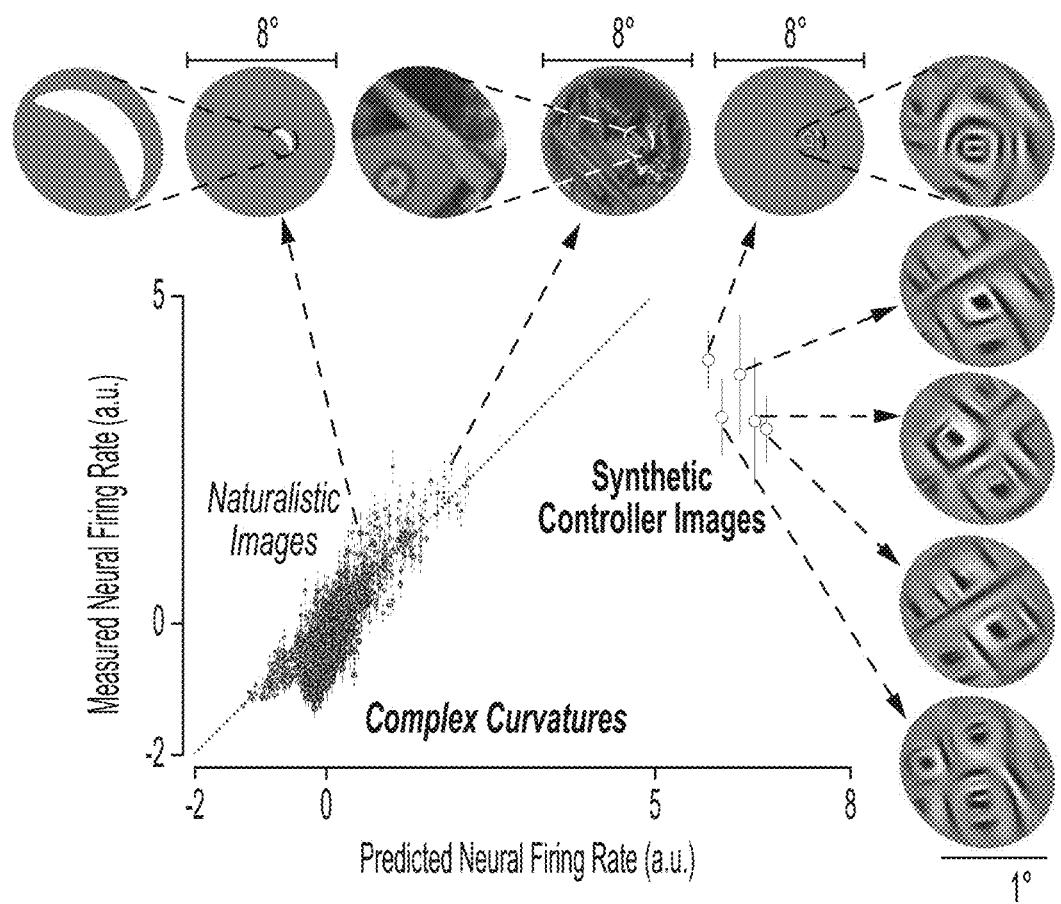
FIG. 6A is an example of measured neural activity for naturalistic images, complex curved stimuli images, and stimulus images configured to drive the firing rate of a target neural site without regulating activity of other measured neural sites, in accordance with some embodiments described herein.

An example of the results of applying the Stretch Control images to the retinae of one monkey to target one of its V4 sites is shown in FIG. 6A, along with the ANN-modelpredicted responses of this site for all tested images (e.g., including naturalistic and complex curvature images), in accordance with some embodiments described herein. FIG. 6A shows normalized activity level of the target V4 neural sites for all of the naturalistic images, complex curved stimuli, and for its five synthetic stretch controller images. The best driving images within each category, and the zoomed view of the receptive field for each, are shown along the top of FIG. 6A.

A closer visual inspection of this neural site's "best" natural and complex curvature images within the site's cRF suggests that it might be especially sensitive to the presence of an angled convex curvature in the middle and a set of concentric circles at the bottom left side. This is consistent with extensive systematic work in V4 using such stimuli, and it suggests that the cRF was successfully located and the stimulus presentation was tuned to maximize neural firing rate by the standards of such prior work. Interestingly, all five synthetic stretch control images were found to drive the neural responses above the response to each and every tested naturalistic image and above the response to each and every complex curvature stimulus presented within the CRF.

Figure 6B:
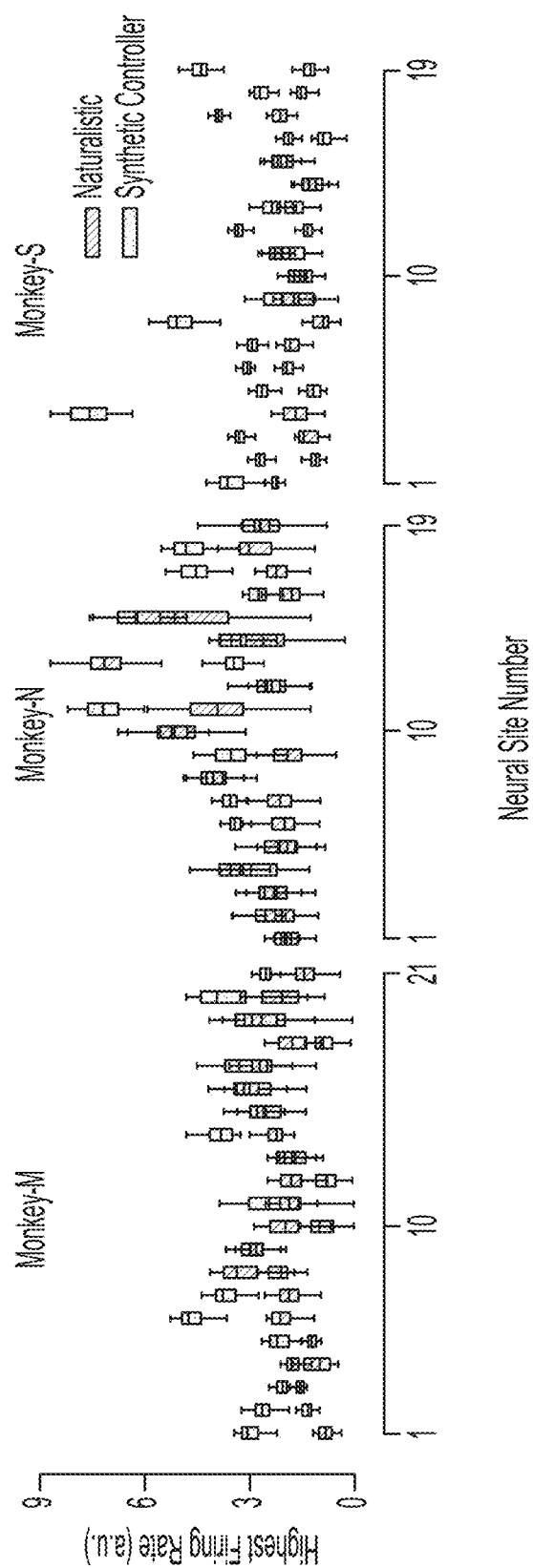
FIG. 6B is data illustrating differences in firing rates in response to naturalistic images and stimulus images configured to drive the firing rate of a target neural site for three subjects, in accordance with some embodiments described herein.

To quantify the goodness of this stretch control, the neural response to the best of the five synthetic images (cross-validated over repeated presentations) was measured and compared with the naturally-observed maximal firing rate. The stretch controller images were found to successfully drive 68% of the V4 neural sites (40 out of 59) statistically beyond their maximal naturally-observed firing rate (unpaired-samples t-test at the level of $p<0.01$ between distribution of highest firing rates for naturalistic and synthetic images; distribution generated from 50 random cross-validation samples). FIG. 6B shows these measured neural firing rates for the targeted neural sites of all three monkey subjects illustrating differences in the neural firing rates of targeted neural sites in response to naturalistic images and stretch controller stimulus images, in accordance with some embodiments described herein. The stretch controller image synthesis was restricted within the receptive field of the target neural site.

Figure 6C:
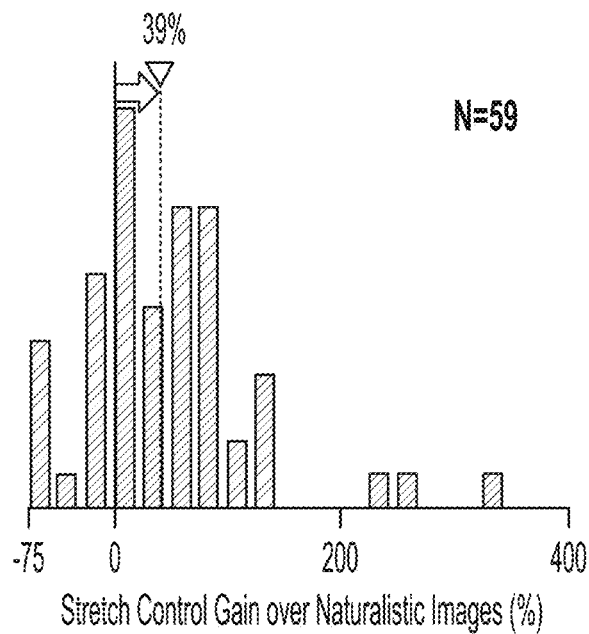
FIG. 6C is data illustrating an increase in the neural firing rate in response to stimulus images configured to drive the firing rate of a target neural site as compared to naturalistic images, in accordance with some embodiments described herein.

Measured as an amplitude, the stretch controller images were found to typically produce a firing rate that was 39% higher than the maximal naturalistic firing rate (median over all tested sites). This amplitude is shown in FIG. 6C, which is a histogram showing an increase in the neural firing rate over naturalistic images for cRF-restricted stretch controller images, in accordance with some embodiments described herein.

Figures 13A, 13B:
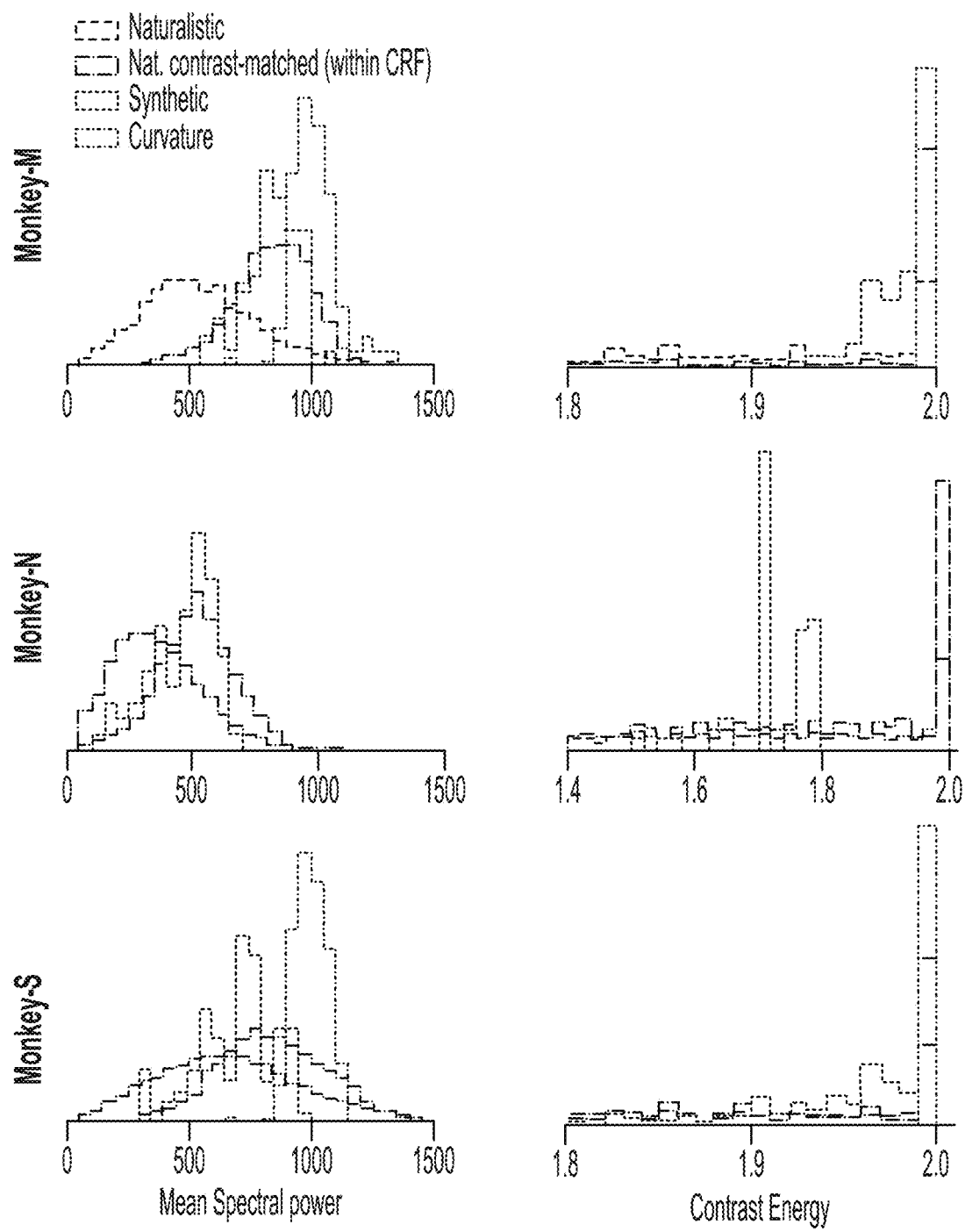
FIG. 13A are examples of distributions of spectral power within the cRFs of three subjects for stimulus images configured to drive the firing rate of a target neural site without regulating activity of other measured neural sites, naturalistic images, contrast-matched naturalistic images, and complex curvature images, in accordance with some embodiments described herein.
FIG. 13B are examples of distribution of contrast energy within the cRFs of three subjects for stimulus images configured to drive the firing rate of a target neural site without regulating activity of other measured neural sites, naturalistic images, contrast-matched naturalistic images, and complex curvature images, in accordance with some embodiments described herein.

Because the fixed set of naturalistic images was not optimized to maximally drive each V4 neural site, the possibility that the stretch controller was simply rediscovering image pixel arrangements that are already known from prior systematic work to be good drivers of V4 neurons was considered. To test this hypothesis, 19 of the V4 sites ($n_M$=11, $n_s$=8) were tested by presenting, inside the cRF of each neural site, each of 370 complex curve shapes. The complex curve shapes have been previously shown to be a stimulus set that contains image features that are good at driving V4 neurons when placed within the cRF. Additionally, the fixed set of naturalistic images were not configured to maximize the local image contrast within each V4 neuron's cRF, the complex curved shapes were displayed at a contrast that was matched to the contrast of the synthetic stretch controller images. FIGS. 13A and 13B are examples of distributions of spectral power and contrast energy, respectively, within the cRFs of the three subjects for synthetic stretch controller images, naturalistic images, contrast-matched naturalistic images, and complex curvature shape images. The spectral power of FIG. 13A was computed using a 2-D fast Fourier transformation and summed in the frequency range of 1-30 cycles/degree. The contrast energy was calculated as the ratio between the maximum and background luminances. For all images, the average luminance was used as the background value. Because the synthetic images consisted of complex visual patterns, the contrast energy was also calculated using an alternative method based on spectral energy within the cRFs. The average power was calculated in the cRF in the frequency range of 1 to 30 cycles per degree. For all tested neural sites, contrast energy values within the cRF for synthetic stretch controller images were less than or equal to the classic, complex-curvature V4 stimuli.

Figure 6D:
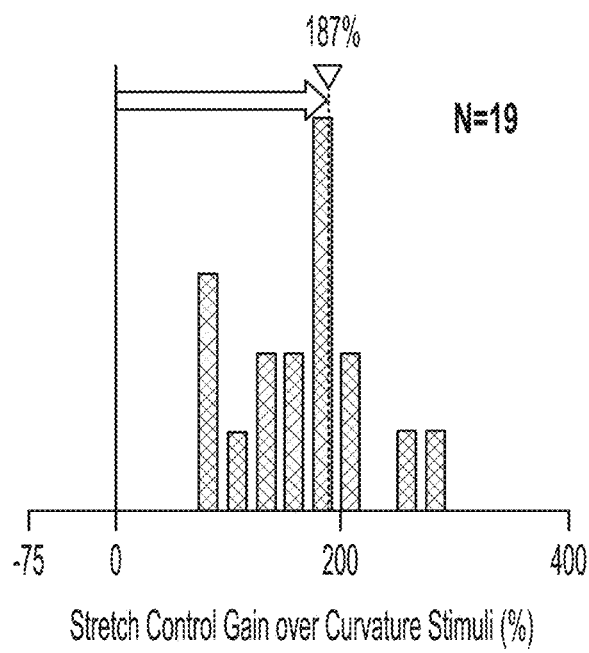
FIG. 6D is data illustrating an increase in the neural firing rate in response to stimulus images configured to drive the firing rate of a target neural site as compared to complex curved stimuli images, in accordance with some embodiments described herein.

It was found that for each tested neural site, the synthetic controller images generated higher firing rates than the most-effective complex curve shape, as seen in FIG. 6D. FIG. 6D is a histogram showing an increase in the neural firing rate in response to stretch controller images over complex curved stimuli images, in accordance with some embodiments described herein. The black triangle with dotted black line marks the median of the scores over all tested neural sites. The arrow highlights the gain of 187% in firing rate in each experiment achieved by the controller images. "N" indicates the number of neural sites included in each experiment. Specifically, when the maximal response over all the complex curve shapes was used as the reference (cross-validated over repeated presentations), the median stretch amplitude was even larger (187%) than when the maximal naturalistic image was used as the reference (73% for the same 19 sites). In sum, the ANN-driven stretch controller had discovered pixel arrangements that were better drivers of V4 neural sites than prior systematic attempts to do so.

Figure 16:
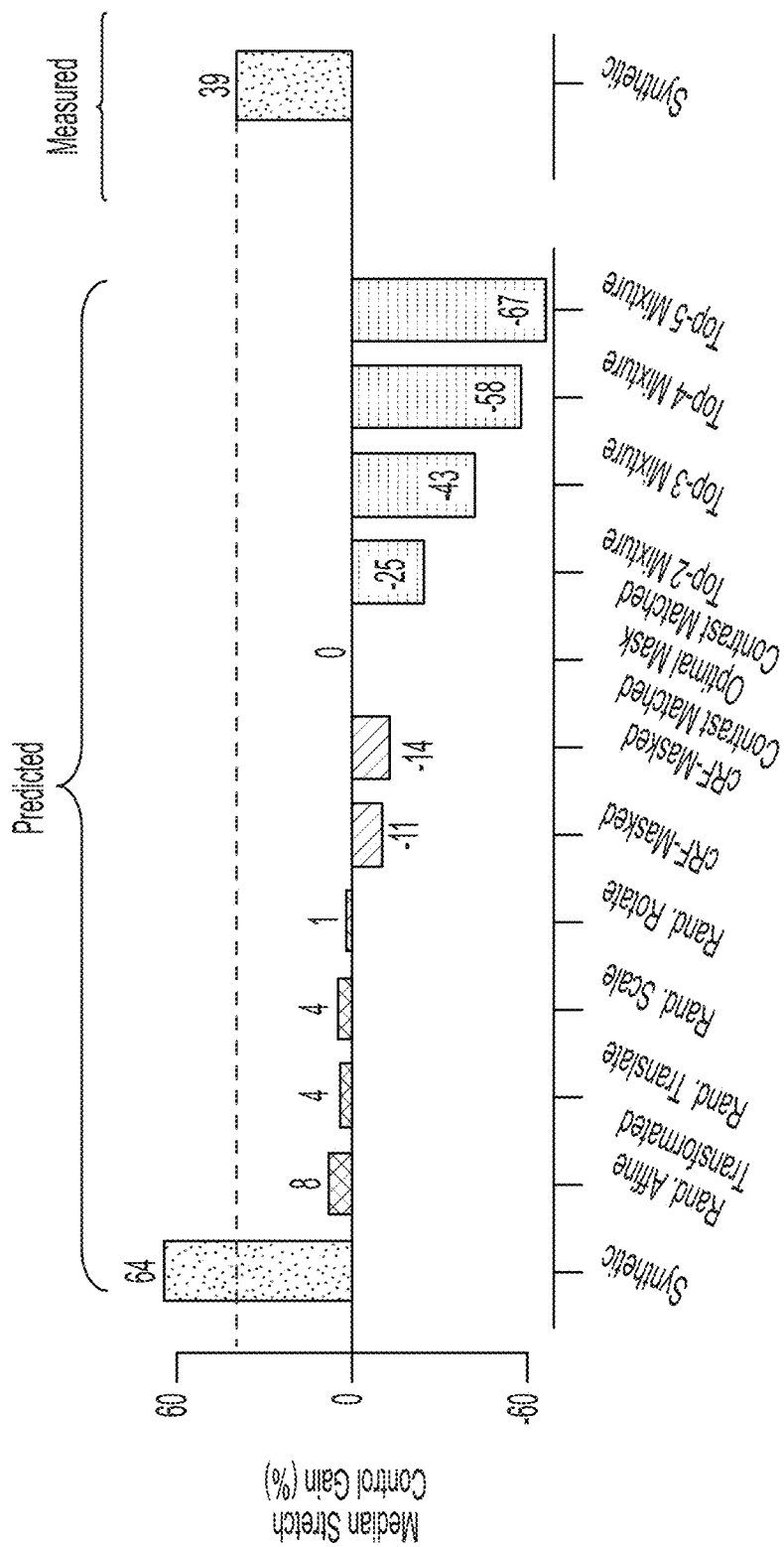
FIG. 16 is a comparison of predicted and measured control gains for stimulus images configured to drive the firing rate of a target neural site without regulating activity of other measured neural sites, affine transformations of naturalistic images, images formed by mask optimization, and images formed by image mixing, in accordance with some embodiments described herein.

To further test the possibility that the relatively simple image transformations might also achieve neural response levels that were as high as the synthetic controller images, simulations were carried out to test the predicted effects of a battery of alternative image manipulations. First, to ask if the response might be increased simply by reducing surround suppression effects, each neural site's predicted response was assessed relative to its best naturalistic image response, spatially cropped to match the site's cRF. Additionally, the contrast of that cropped image was adjusted to match the average contrast of the synthetic images for the site (also measured within the site's cRF). Over all tested sites, the predicted median stretch control gain achieved using these newly generated images was 14% lower than the original naturalistic set (n=59 sites). FIG. 16 shows this comparison of predicted and measured control gains for stretch controller images, affine transformations of naturalistic images, images formed by mask optimization, and images formed by image mixing. Results on the left "Predicted" panel were computed using the model predictions for each case. The "Measured" bar plot on the right indicates the achieved stretch control gain using the synthesis procedure as described herein. Each bar indicates the median stretch control gain over the naturalistic image set.

To explore this further, the size and location of the cropped region of the natural image was improved. The stretch control gain achieved with this procedure was 0.1% lower than that obtained for the original naturalistic images. Second, response-optimized affine transformations of the best naturalistic images (position, scale, rotations) were tested. Third, to place some energy from multiple features of natural images in the cRF, contrast blends of the best 2-5 images for each site were tested. The predicted stretch control gain of each of these manipulations was still far below that achieved with the synthetic controller images. In summary, the achieved stretch control ability is non-trivial in that, even at high contrast, it cannot be achieved by: simple curvature features, simple transformation on naturalistic images, combining good naturalistic images, or optimizing the spatial extent of the image, as shown in FIG. 16.

II. "One-Hot-Population" Control: Activating Only One of Many V4 Neural Sites Similar to prior single unit visual neurophysiology studies, the stretch control experiment attempted to optimize the response of each V4 neural site one at a time without regard to the rest of the neural population. But the ANN model potentially enables much richer forms of population control in which each neural site might be independently controlled. As a first test of this, the synthesis algorithm was asked to try to generate controller images with the goal of driving the response of only one "target" neural site high while simultaneously keeping the responses of all other recorded neural sites low (aka a "one-hot" population activity state).

This one-hot-population control was tested on neural populations in which all sites were simultaneously recorded (One-hot-population Experiment 1; n=38 in monkey-M; Experiment 2; n=19 in monkey-S). Specifically, a subset of neural sites as "target" sites was chosen (14 in monkey-M and 19 in monkey-S) and the synthesis algorithm was configured to generate five one-hot-population controller images for each of these sites (e.g., 33 tests in which each test was configured to maximize the activity of one site while suppressing the activity of all other measured sites from the same monkey). For these control tests, the controller algorithm was allowed to optimize pixels over the entire 8° diameter image (that included the cRFs of all the recorded neural sites, see FIGS. 7A-7E), and the one-hot-population controller images were then applied to the monkey retinae to assess the goodness of neural control. The synthesis procedure predicted a softmax score of at least 0.5 for 77% of population experiments (as a reference, the maximum softmax score is 1 and is obtained when only the target neural site is active and all off-target neural sites are completely inactive; for an example near 0.3 see FIGS. 7A-7E).

Figure 7A:
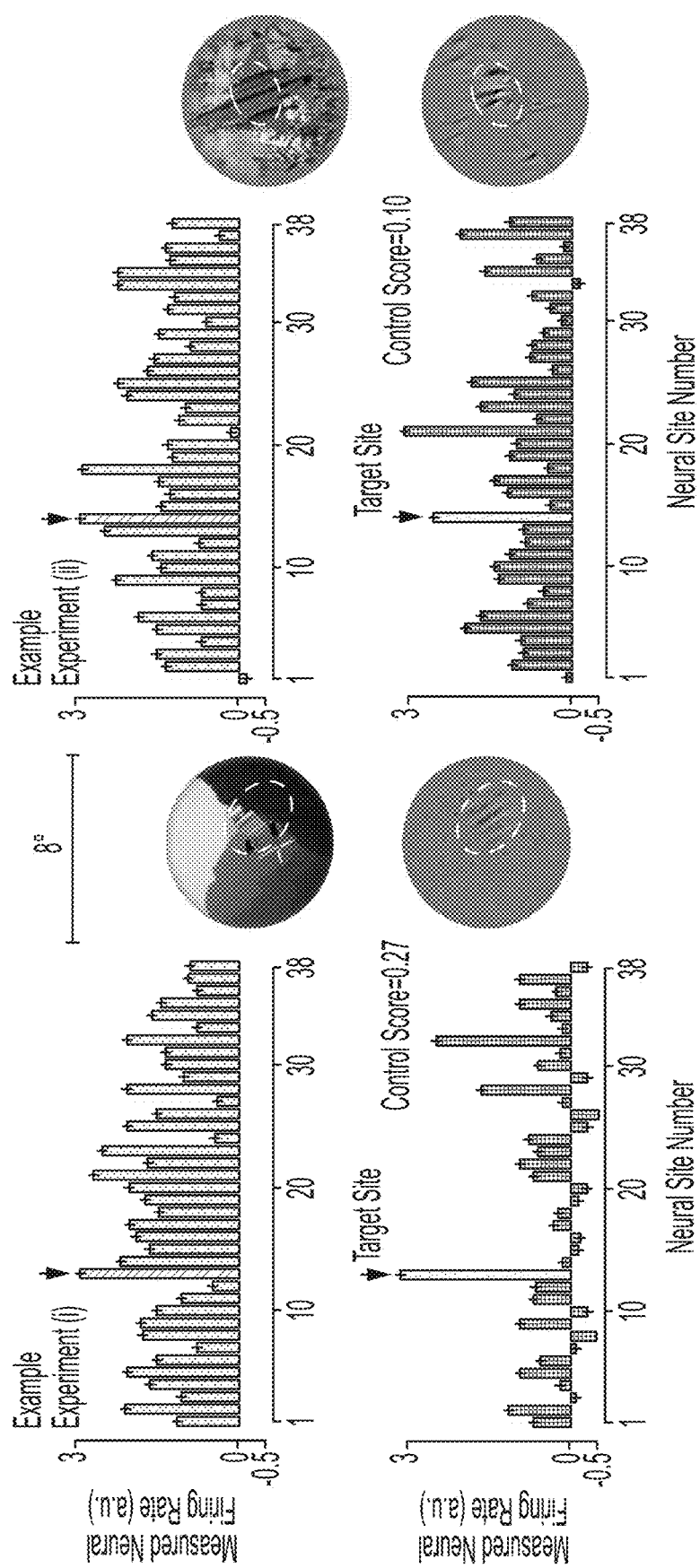
FIG. 7A is data illustrating two experiments comparing neural site responses to naturalized images and stimulus images configured to drive the firing rate of a target neural site and suppress activity of other measured neural sites, in accordance with some embodiments described herein.

While the one-hot-population controller images were found to achieve enhancements in the activity of the target site without generating much increase in off-target sites relative to the neural responses to naturalistic images. Examples are shown in FIG. 7A, which illustrates two experiments (left and right) comparing neural site responses to the "best" naturalized images (top) and one-hot-population stimulus images (bottom), in accordance with some embodiments described herein. In each case, the neural activity of each of the validated V4 sites in the recorded population are plotted, with the target V4 site indicated by an arrow. Note that responses were normalized individually on a normalizer image set to make side-by-side comparison of the responses meaningful. The dashed lines in the naturalistic and synthesized images marks the extended receptive field (within 2-std) of each targeted neural site.

Figure 7B:
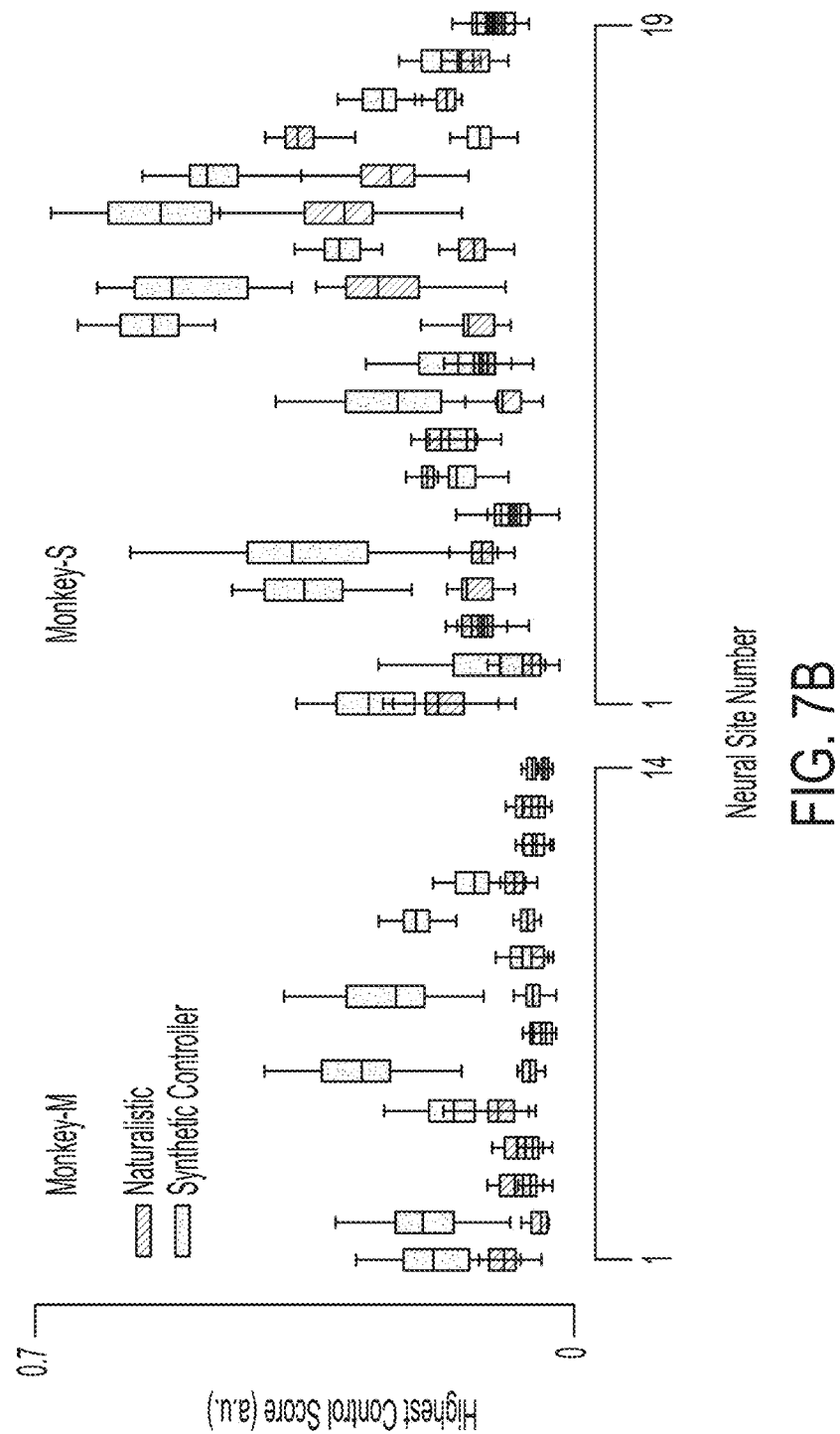
FIG. 7B is data illustrating control scores for naturalistic images and stimulus images configured to drive the firing rate of a target neural site and suppress activity of other measured neural sites for two subjects, in accordance with some embodiments described herein.
Figure 7C:
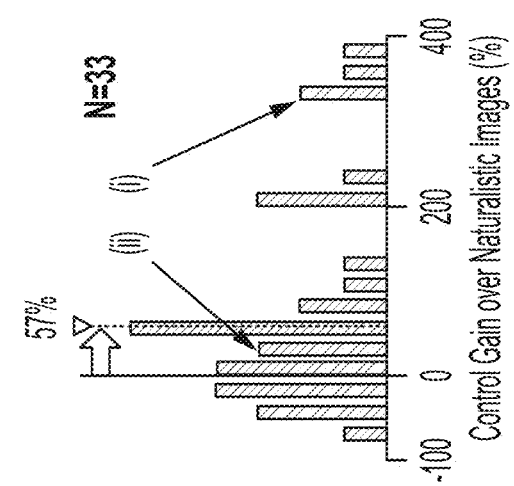
FIG. 7C is a histogram illustrating control gain for the results illustrated in FIG. 7B, in accordance with some embodiments described herein.
Figure 7C:
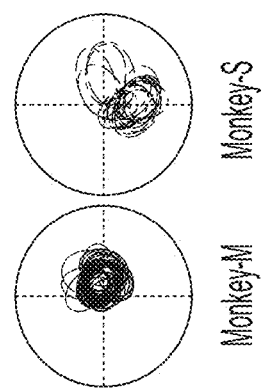

To quantify the goodness of one-hot-population control in each of the 33 tests, one-hot-population score was computed based on the responses of the activity profile of each population (softmax score), and that score was referenced to the one-hot-population control score that could be achieved using only the naturalistic images (e.g., without the benefit of the ANN model and synthesis algorithm). The ratio of those two scores was used as the measure of improved one-hot population control, and it was found that the controller typically achieved an improvement of 57% (median over all 33 one-hot-population control tests), as shown in FIGS. 7B and 7C. Further, it was found that that improved control was statistically significant for 76% of the one-hot population control tests (25 out of 33 tests; unpaired-samples t-test at the level of $p<0.01$).

FIG. 7B shows a distribution of control scores for "best" synthetic one hot population control images and naturalistic images for all 33 one hot population full-image controller experiments ($n_M=14$, $n_s=19$). The control scores were computed using cross-validation as described herein. FIG. 7C is a histogram illustrating one hot population control gain for the results illustrated in FIG. 7B, and shows an improvement in neural firing over naturalistic images. The markers of (i) and (ii) indicate the scores corresponding to example experiments shown in FIG. 7A.

Figure 7D:
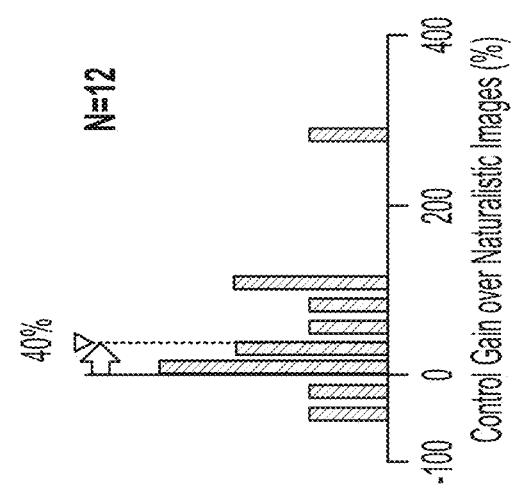
FIG. 7D is a histogram illustrating control gain for the results illustrated in FIG. 7B and analyzed so that all neural sites have highly overlapping classical receptive fields (cRFs), in accordance with some embodiments described herein.
Figure 7D:
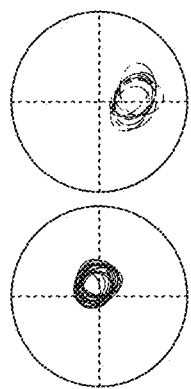

The possibility that the improved population control was resulting from the non-overlapping cRFs that would allow neural sites to be independently controlled by restricting image contrast energy to each site's cRF was also considered. To test this possibility, a sub-sample of the measured neural population in which all sites had strongly overlapping cRFs was analyzed, as shown in FIG. 7D, which is a histogram illustrating control gain for the results illustrated in FIG. 7B but analyzed for sub-populations selected so that all neural sites have highly overlapping cRFs. A neural population of size 10 was considered in monkey-M and of size 8 in monkey-S for this experiment with largely overlapping cRFs. The experiment was performed on 12 target neural sites in two monkeys (4 in monkey-M and 8 in monkey-S) and it was found that the amplitude of improved control was still 40%. Thus, a large portion of the improved control may be the result of specific spatial arrangements of luminous power within the retinal input region shared by multiple V4 neural sites that the ANN-model has implicitly captured and predicted and the synthesis algorithm has successfully recovered.

Figure 8:
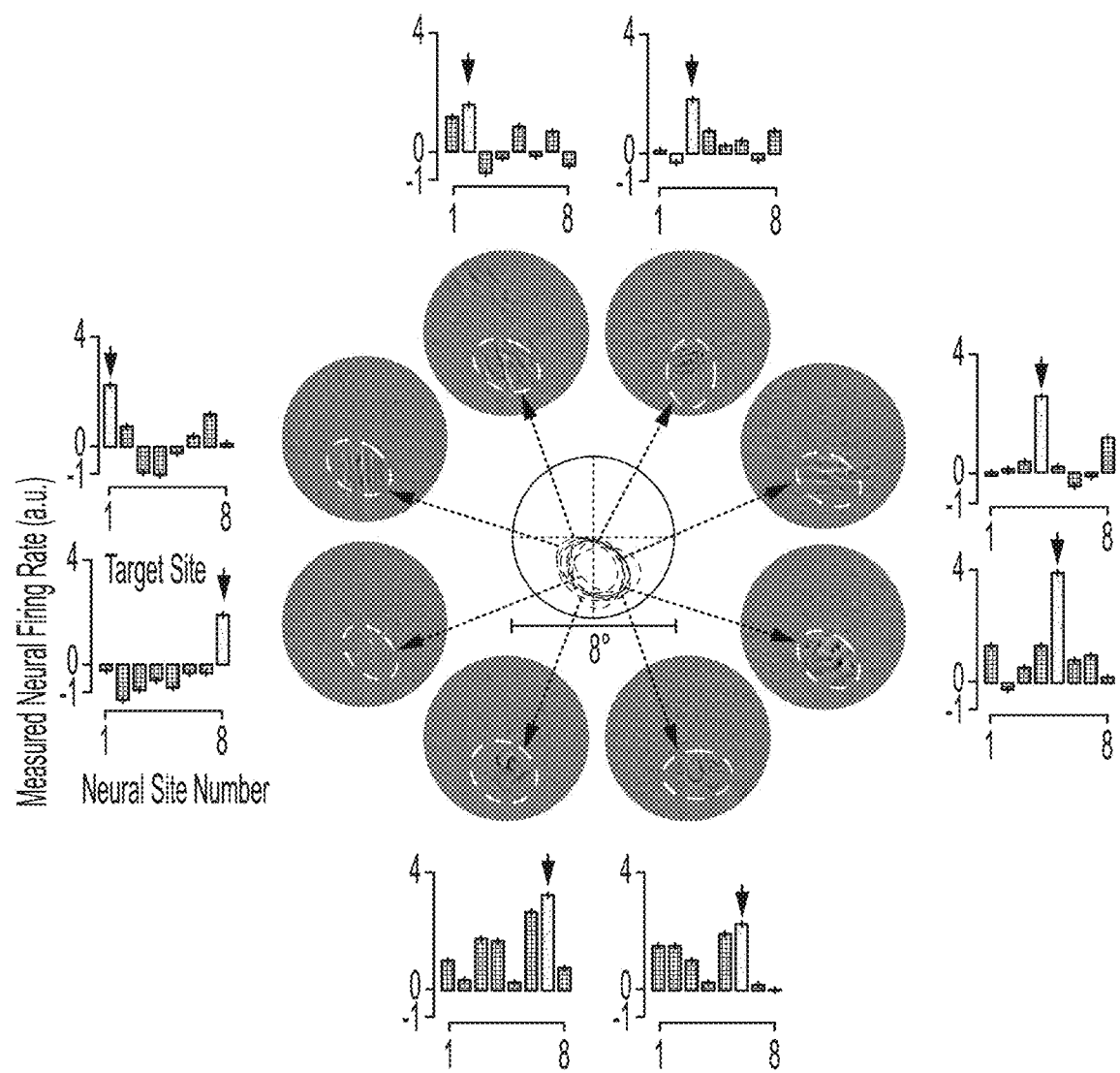
FIG. 8 is data illustrating independent control of neural sites with overlapping cRFs and corresponding stimulus images, in accordance with some embodiments described herein.

FIG. 8 shows data illustrating such independent control of neural sites with overlapping cRFs and corresponding stimulus images, in accordance with some embodiments described herein. The controller images shown in FIG. 8 were synthesized to try to achieve one hot population control over a population of eight neural sites. For each control test, the target neural site is indicated by an arrow. Despite highly overlapping receptive fields (e.g., as shown in the center image of FIG. 8), most of the neural sites could be individually controlled. The controller images are shown surrounding the center overlapping cRFs along with the extended cRF (2-std) of each site (dashed lines).

Figure 9:
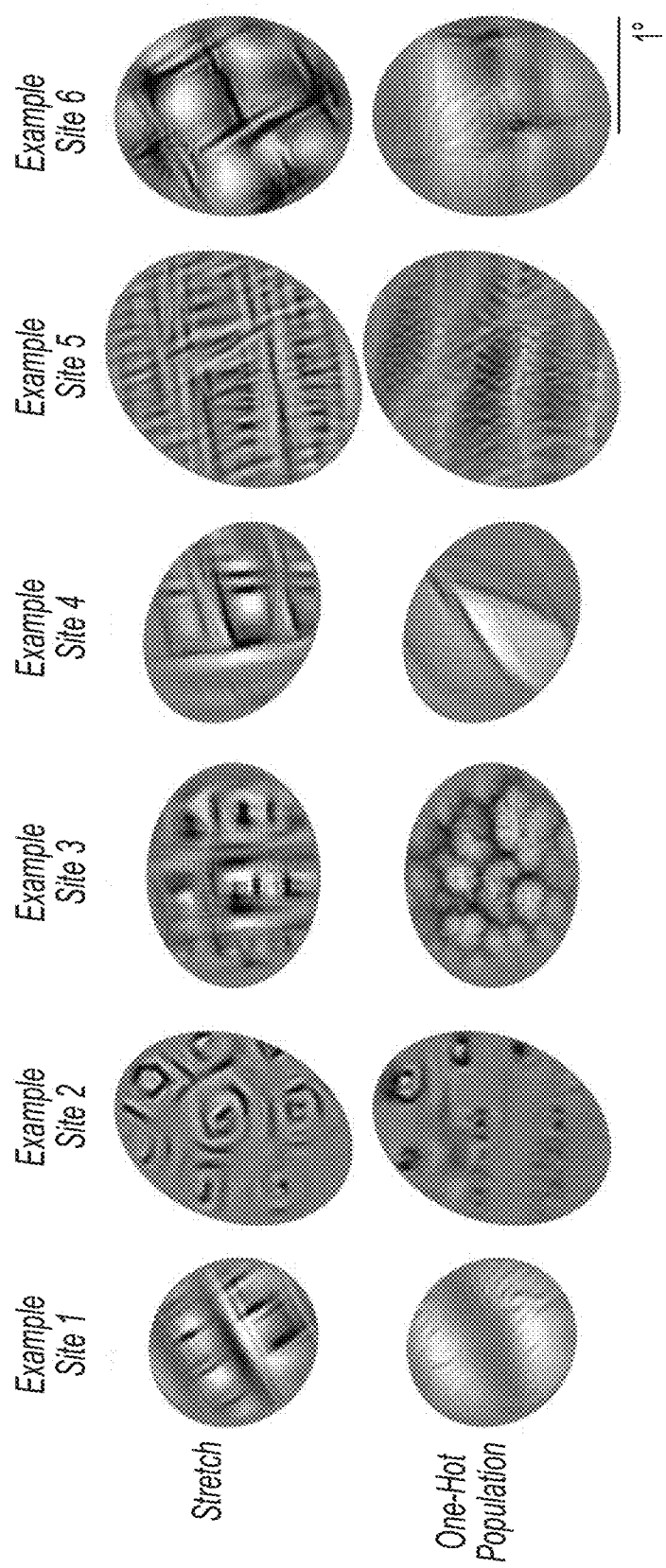
FIG. 9 shows examples of stimulus images configured to drive the firing rate of a target neural site without regulating activity of other measured neural sites and stimulus images configured to drive the firing rate of a target neural site and suppress activity of other measured neural sites for several neural sites, in accordance with some embodiments described herein.

FIG. 9 shows example controller images synthesized in "stretch" and "one-hot population" settings for six example target neural sites. The controller images were synthesized from the same initial random image, but optimized for each target neural site and for each control goal ("stretch" or "one-hot population" as described herein). Visual inspection suggests that, for each target site, the one-hot population control images contain only some aspects of the image features in the stretch images.

Figure 11:
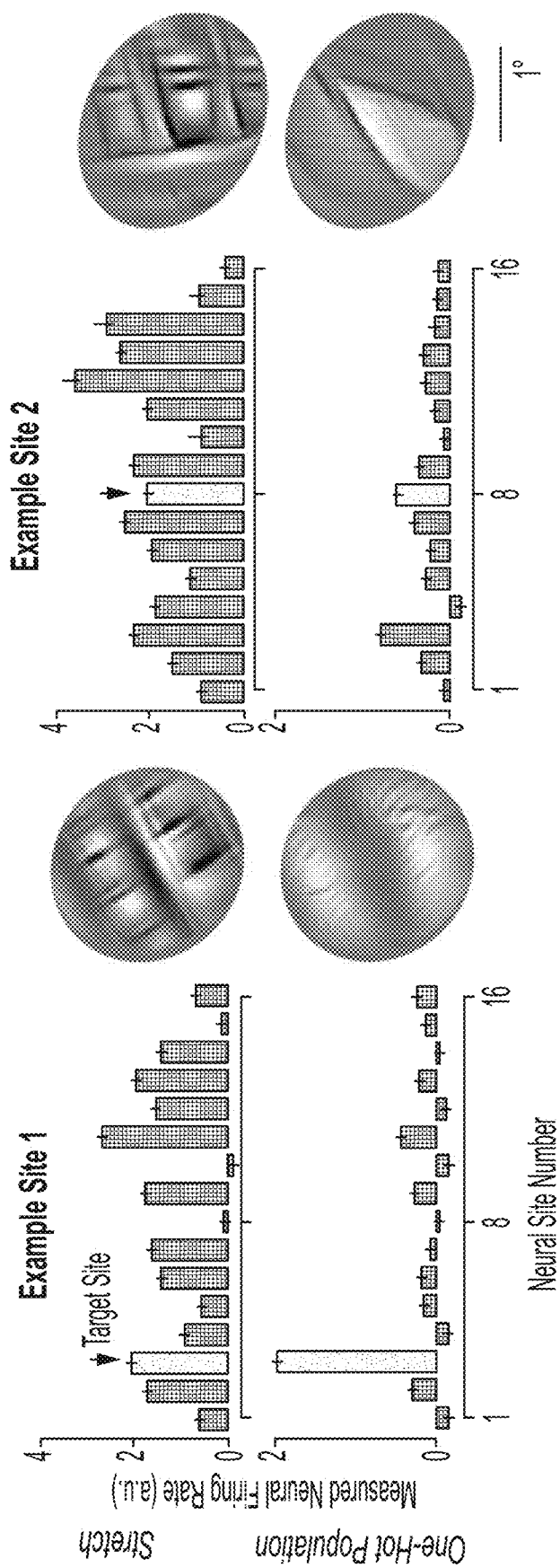
FIG. 11 is data showing neural responses for a number of neural sites in response to stimulus images configured to target two particular neural sites, the stimulus images being configured to drive the firing rate of a target neural site without regulating activity of other measured neural sites and being configured to drive the firing rate of a target neural site and suppress activity of other measured neural sites, in accordance with some embodiments described herein.

FIG. 11 shows a comparison of population response in stretch and one-hot population settings, in accordance with some embodiments described herein. The population responses in stretch and one-hot population settings are demonstrated for two example neural sites (left and right panels). The one-hot population images were generated with an objective function including 16 neural sites with highly overlapping receptive fields. Compared to the stretch controller images, the one-hot-population images have fewer identifiable features. The displayed images were synthesized using the same initial random image.

Figure 7E:
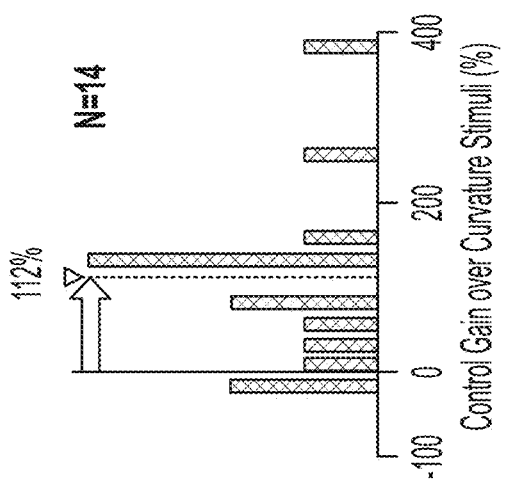
FIG. 7E is a histogram illustrating control gain relative to complex curvature stimulus, in accordance with some embodiments described herein.
Figure 7E:
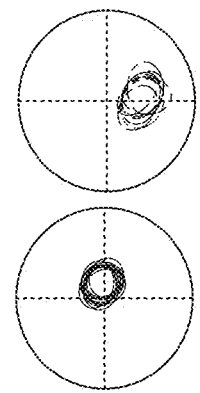

As another test of one-hot-population control, an additional set of experiments was conducted in which the one-hot control synthesis algorithm was restricted to operate only on image pixels within the shared cRF of all neural sites in a sub-population with overlapping cRFs. These results for within-cRF synthetic one-hot population control were compared with the within-cRF one-hot population control that could be achieved with the complex curved shapes as prior experiments with these stimuli were also designed to manipulate V4 responses only using pixels inside the cRF. It was found that, for the same set of neural sites, the synthetic controller images produced a very large one-hot population control gain and the control score was significantly higher than best curvature stimulus for 86% of the neural sites (12 out of 14). FIG. 7E shows a histogram illustrating one hot population control gain relative to best complex curvature stimulus in the shared cRF and the controller algorithm was restricted to operate only in that shared cRF (n=14), and shows a 112% increase in control gain.

III. Generalizing the Functional Fidelity of the ANN Brain Model to Novel Images In addition to testing non-invasive causal neural control, these experiments also aimed to determine if ANN models would pass a stronger test of functional similarity to the brain.

Specifically, does that model-to-brain similarity generalize to entirely novel images? Because the controller images were synthesized anew from a random pixel arrangement and were optimized to drive the firing rates of V4 neural sites both upwards (targets) and downwards (one-hot-population off-targets), they are considered to be a potentially novel set of neural-modulating images that is far removed from naturalistic images. This hypothesis was quantified and confirmed by demonstrating that the synthetic images were indeed statistically farther from the naturalistic images compared to the naturalistic image set to itself by measuring distances in pixels space, recorded V4 neural population space, and model-predicted V4 population space.

These measured distances are shown in FIGS. 15A through 15E. Each distribution plots a minimum distance of each of the images in the test set to the full set of 640 naturalistic images (e.g., a minimum over 640). In each case, the reference is the minimum distance of any given naturalistic image to the other naturalistic images. Note that, in all cases, the synthetic images are farther from the naturalistic images than affine transformations of the naturalistic images. FIGS. 15A and 15B show pixel-space distances within the receptive field of each neural site. The random affine transformations naturalistic image set was generated by randomly performing combinations of scaling, translation and rotation transformations on random naturalistic images for n=640. FIGS. 15C and 15D show Euclidean distances in the predicted V4 population response space ($n_M=21$, $n_N=19$, and $n_s=19$ simulated V4 neural sites). FIG. 15E shows Euclidean distances in measured neural population responses ($n_M=21$, $n_N=19$, and $n_s=19$ actual V4 neural sites). FIG. 15F shows a scatter plot of the 640 naturalistic images and 285 synthetic images where the axes are the first two principle components of the measured V4 population response space (using Multi-Dimensional Scaling; data from Monkey-S).

To ask how well the V4 predictor model generalizes to these novel synthetic images, for each neural site the predicted response was compared to every tested synthetic image with the actual neural response, using the same similarity measure as prior work, but now with zero parameters to fit. That is, a good model-to-brain similarity score required that the ANN predictor model for each V4 neural site accurately predict the response of that neural site for all of many synthetic images that are each very different than those that were used to train the ANN (photographs) and also very different from the images used to map ANN "V4" sites to individual V4 neural sites (naturalistic images).

Figure 12A:
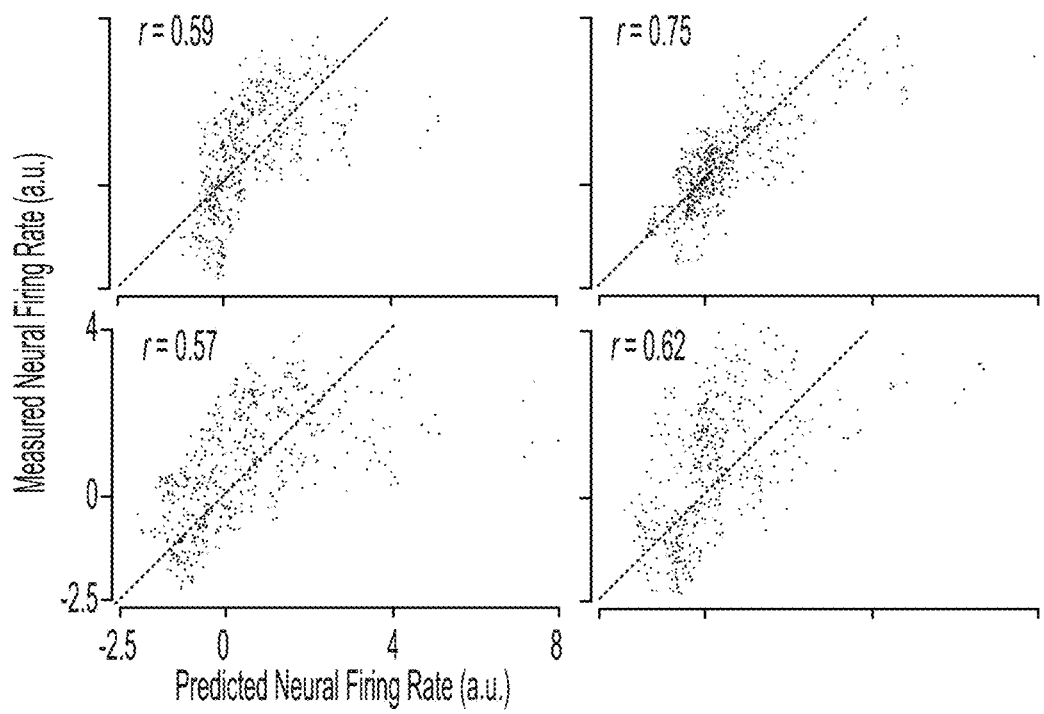
FIG. 12A illustrates predicted and measured V4 neural responses to stimulus images for four example neural sites, in accordance with some embodiments described herein.
Figure 12B:
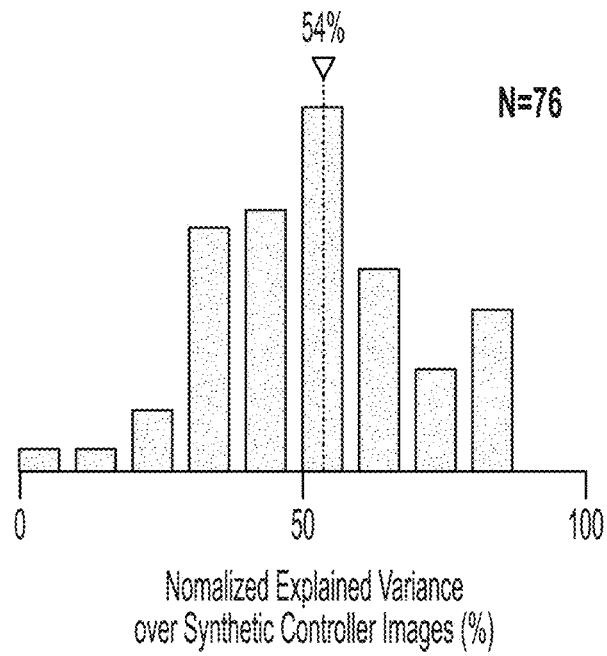
FIG. 12B is a histogram showing normalized explained variance over stimulus images for all tested neural sites across three subjects, in accordance with some embodiments described herein.

Consistent with the control results, it was found that the ANN model accounted for 54% of the explainable variance for the set of synthetic images (median over 76 neural sites in three monkeys). FIG. 12A shows four scatter plots of predicted and measured V4 neural responses to synthetic stimulus images for four example neural sites. For most target neural sites, the predicted and measured neural responses were significantly correlated. Each dot represents the prediction and average measured response to a single image. FIG. 12B is a histogram showing normalized explained variance over stimulus images for all tested neural sites across three subjects. The model accounted for 54% (median across all tested neural sites in three monkeys; N=76) of the explainable variance.

While the model may overestimate the neural responses to synthesized stimuli on some occasions and the model-to-brain similarity score is somewhat lower than that obtained for naturalistic images responses (89%), the model still predicts a substantial portion of the variance considering the fact that all parameters were fixed to make these "out-of-naturalistic-domain" image predictions. This may therefore be the strongest test of generalization of today's ANN models of the ventral stream thus far, and it again shows that the model's internal neural representation is both remarkably similar to the brain's intermediate ventral stream representation (V4), but also that it is still not a perfect model of the representation. Additionally, because the synthetic images were generated by the model, the accuracy of predictions cannot be assessed for images that are entirely "out-of-model-domain."

In sum, it is demonstrated herein that, using a deep ANN-driven controller method, the firing rates of most V4 neural sites may be pushed beyond naturally occurring levels and that V4 neural sites with overlapping receptive fields may be partly independently controlled. In both cases, the goodness of this control is shown to be unprecedented in that it is superior to that which can be obtained without the ANN. Finally, it is found that, with no parameter tuning, the ANN model generalizes quite well to predict V4 responses to synthetic images. These images are strikingly different than the real-world photographs used to tune the ANN synaptic connectivity and map the ANN's "V4" to each V4 neural site.

Decades of visual neuroscience research has closely equated an understanding of how the brain represents the external visual world with an understanding of what stimuli cause each neuron to respond the most. Indeed, textbooks and important recent results describe that V1 neurons are tuned to oriented bars, V2 neurons are tuned to correlated combinations of V1 neurons found in natural images, V4 neurons are tuned to complex curvature shapes in both 2D and 3D and tuned to boundary information, and IT neurons respond to complex object-like patterns including faces and bodies as special cases.

While these efforts have been helpful to building both a solid foundation and intuitions about the role of neurons in encoding visual information, the results herein show how they can be further refined by current and future ANN models of the ventral stream. For instance here it is found that synthesis of only few images leads to higher neural response levels that was possible by searching in a relatively large space of natural images (n=640) and complex curved stimuli (n=370) derived from those prior intuitions. This shows that even today's ANN models already provide a new ability to find manifolds of more optimal stimuli for each neural site at a much finer degree of granularity and to discover such stimuli unconstrained by human intuition and difficult to fully describe by human spoken language (see examples in FIG. 10). This is likely to be especially important in mid and later stages of the visual hierarchy (e.g. in V4 and inferior temporal cortex) where the response complexity and larger receptive fields of neurons makes manual search intractable.

The results presented herein show how today's ANN models of the ventral stream can already be used to achieve improved non-invasive, population control (e.g., FIG. 8). However, in the one-hot population control setting every one of the responses of the "off-target" neural sites were not able to be suppressed while keeping the target neural site active (see examples in FIGS. 7A-7E and 8). Post-hoc analysis showed that these off-target neural sites could partially be anticipated, and they were typically the sites that had high patterns of response similarity with the target site (r=0.49, p<10−4; correlation between response similarity with the target neural site over naturalistic images and the off-target activity level in the full image one-hot population experiments; n=37 off-target sites). Such results raise interesting scientific and applied questions of if and when perfect independent control is possible at neuron-level resolution. Are the current limitations on control due to anatomical connectivity that restricts the potential population control, the non-perfect accuracy of the current ANN models of the ventral stream, non-perfect mapping of the model neurons to the individual neural site in the brain, the fact that we are attempting to control multi-unit activity, inadequacy of the controller image synthesis algorithm, or some combination of all of these and other factors?

Consider the synthesis algorithm: intuitively, each particular neural site might be sensitive to many image features, but maybe only to a few that the other neural sites are not sensitive to. This intuition is consistent with the observation that, using the current ANN model, it was more difficult for the synthesis algorithm to find good controller images in the one-hot-population setting than in the stretch setting (the one-hot-population optimization typically took more than twice as many steps to find a synthetic image that is predicted to drive the target neural site response to the same level as in the stretch setting), and visual inspection of the images suggests that the one-hot-population images have fewer identifiable "features" (e.g., as seen in FIGS. 9 and 11). As the size of the to-be-controlled neural population is increased, it would likely become increasingly difficult to achieve fully independent control.

Figure 14:
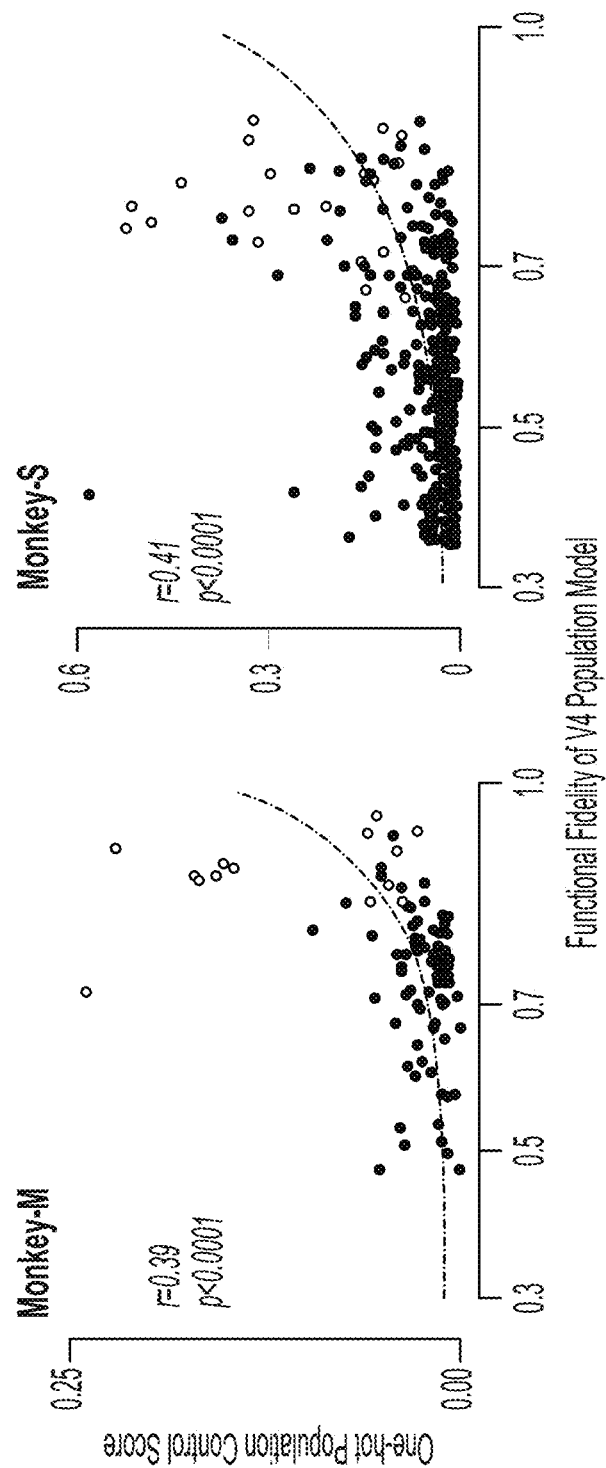
FIG. 14 shows, for two subjects, functional fidelity of a V4 population model plotted against the control score achieved using the V4 population model for stimulus images configured to drive the firing rate of a target neural site and suppress activity of other measured neural sites, in accordance with some embodiments described herein.

Consider the current ANN models: the data herein suggest that future improved ANN models are likely to enable even better control. For example, better ANN V4 population predictor models generally produced better one-hot population control of that V4 population. FIG. 14 shows, for two subjects (left and right panels), functional fidelity of a V4 population model plotted against the control score achieved using the V4 population model for stretch controller images. Higher functional fidelity models may increase the ability to control neural responses. The one-hot population control score was evaluated for each target neural site in each monkey subject for a range of possible models with different prediction accuracy levels. In each monkey session, the functional fidelity of a V4 population model (measured by the mean of: 1) explained variance of target neural site and 2) the mean of the explained variance for all the off-target sites) was plotted against the one-hot population control score achieved with that population model. It was found that these were significantly correlated as assessed by Spearman rank order correlation, shown on each panel. For this analysis, for each target neural site, the original tests and also tests in which the predictive model of the target neural site was swapped with the model of randomly-chosen off-target site were included. Both tests were included in order to "mismatch" the tests as an example of what would have happened in the experiment if the synthesis algorithm had been given the wrong models (e.g., it would have produced one hot population control stimuli that were already tested, so the resulting control score can be computed without doing new recording experiments). The functional fidelity of the V4 population model was assessed using the mismatched models and the population control score achieved using the new population model's synthetic control images (again, from population responses to images that were already tested). Open circles correspond to cases where the target neural site's model and responses were matched (e.g., results of the original one hot population tests), and black dots correspond to the cases where they were mismatched. The dashed line shows an exponential function fitted to the data points, highlighting the tendency for higher model fidelity to support better control. Improved ANN models of the ventral visual stream have led to control of high-level neural populations that were previously out of reach. With continuing improvement of the fidelity of ANN models of the ventral stream, the results presented here have likely only scratched the surface on what is possible with such implemented characterizations of the brain's neural networks.

IV. Modulation of Precepts and Emotion-Related States

In some embodiments, targeted neural control may extend beyond control of neural firing rates to cause modulations of percepts and/or emotion-related states, as described herein. Advances in the ability to non-invasively (e.g., through visual stimuli), but precisely, shape the patterns of activity in neural sub-populations may translate into advances in an ability to non-invasively, yet precisely, modulate, induce, or even enhance, a subject's perceptual and/or mental state.

A. Model-Driven Modulation of Perceptual States

Using variants of the "controller image" synthesis strategy described herein, it may be possible to induce changes in perceptual and/or mental states of a subject. These perceptual and/or mental state changes were tested herein. A primary goal was to induce percepts of an object category that are far stronger than can be achieved with natural images. Two measures of perceptual strength were used to evaluate the tests.

Figure 18A:
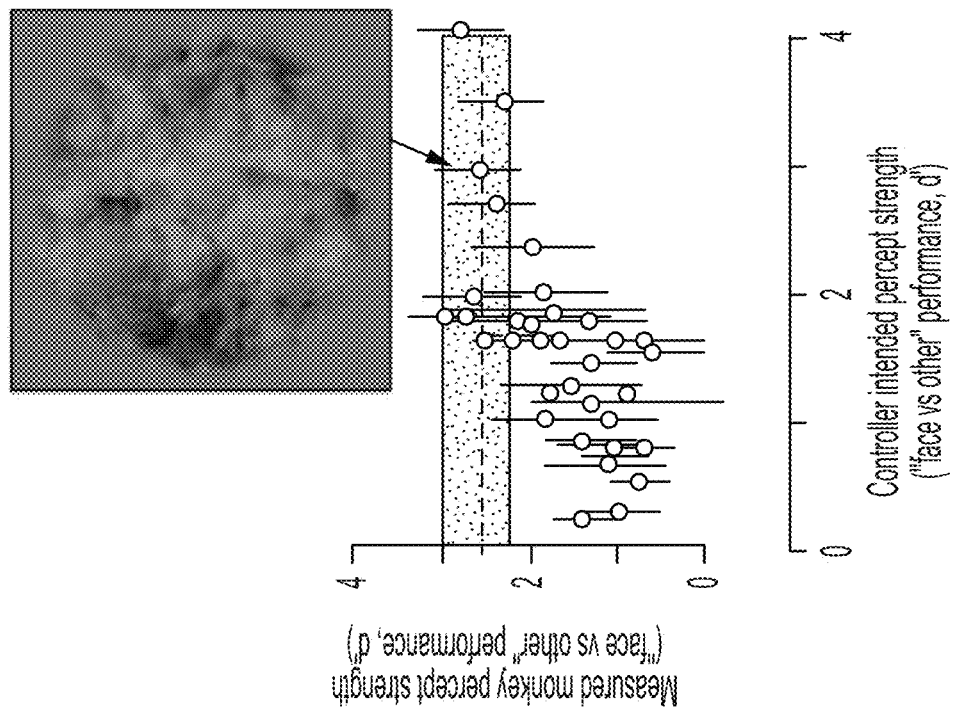
FIG. 18A depicts an object choice task performed by primate subjects and a comparison of model-predicted perceptual strength and measured perceptual strength for synthesized stimulus images, in accordance with some embodiments described herein.
Figure 18A:
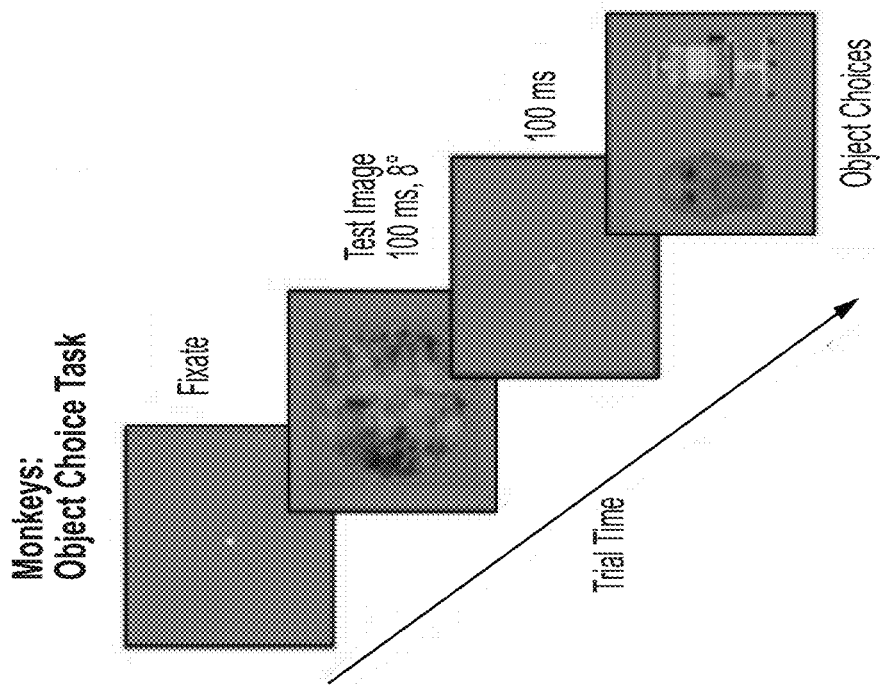

First, using 20 basic object categories, human and monkey subjects were tasked with performing object discrimination tasks in which a test image is followed by a choice of two possible objects. Test images were interleaved with ground truth images and the bias-corrected choice ratio provided a quantitative measure of the perceptual strength (d') along each of the pairwise axes (e.g. that test image was more "face-like" than "carlike"). Examples of such tasks as presented to monkey subjects are shown in the left panel of FIG. 18A. The right panel of FIG. 18A shows a comparison of model-predicted perceptual strength and measured perceptual strength for synthesized controller images (controller start: pixel noise). Note that the controller can generate images from noise that induce face percepts that are as strong as those from a representative face image set.

Figure 18B:
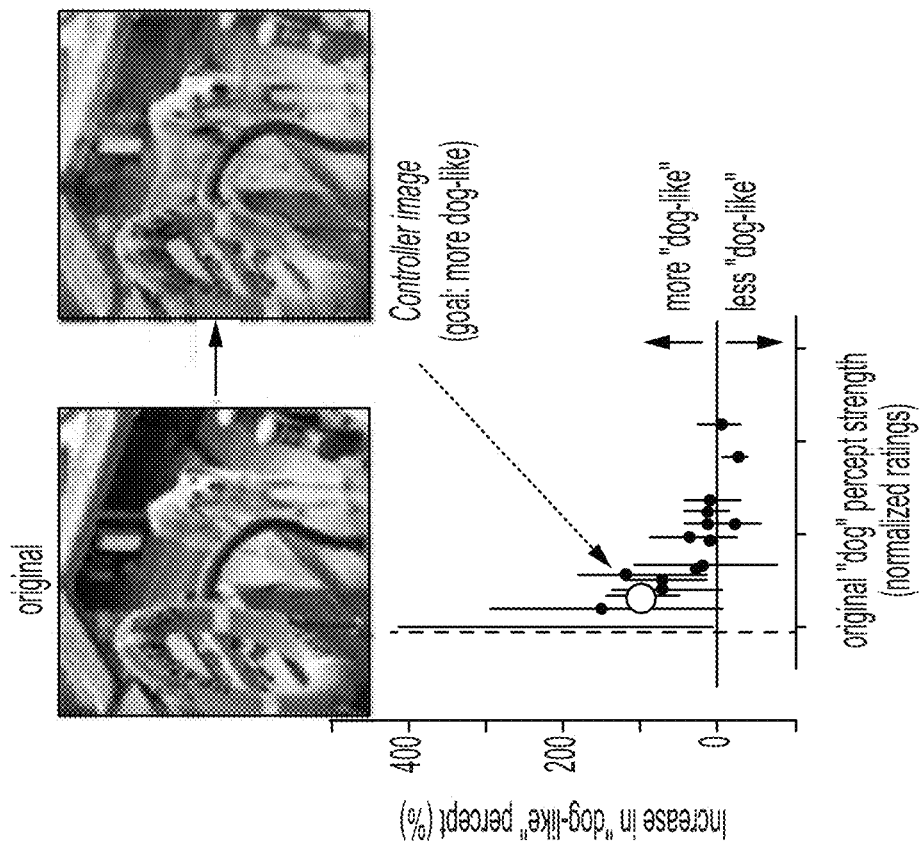
FIG. 18B depicts subjective rating by human subjects of object percept strength in synthesized stimulus images, in accordance with some embodiments described herein.

Second, human subjects were asked to rate the subjective magnitude of their percept of each image. For example, how "bird-like" was a test image, as shown in the left panel of FIG. 18B. The right panel of FIG. 18B shows results for true images of dogs where the controller was asked to increase the perceptual strength of those images (perceptual "stretch"). For many images, the controller succeeded (e.g., the larger datapoint is an example of a more "dog-like" image created by the controller), but not yet for all natural images.

This data in humans and monkeys shows partial success in inducing object percepts from noise images (FIG. 18A) and in improving the perceptual strength of natural images that already contain those objects (FIG. 18B).

B. Model-Driven Modulation of Valence and Arousal States

Figure 19A:
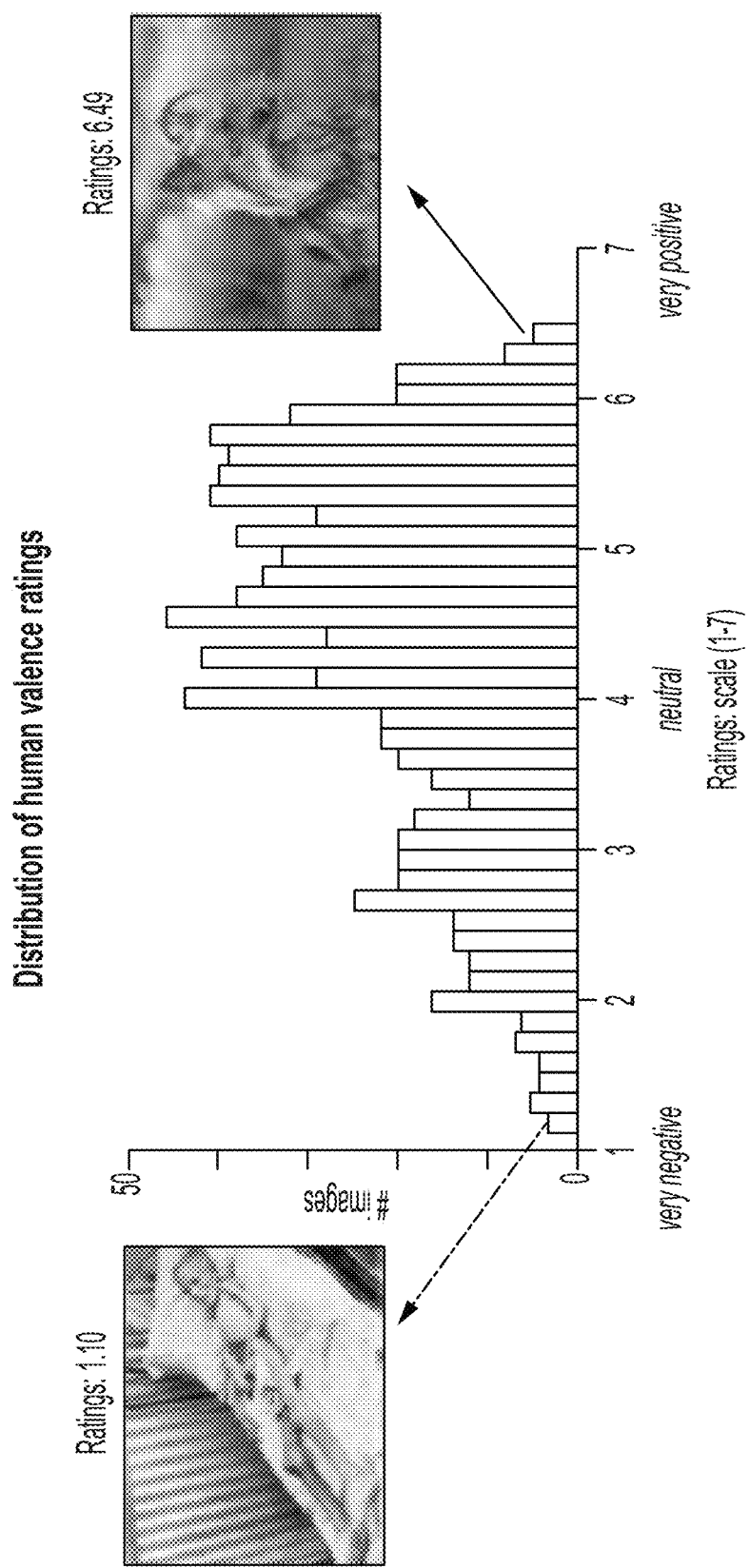
FIG. 19A depicts human subject valence ratings of a series of images with two example images, in accordance with some embodiments described herein.

Another goal was to synthesize novel images that predictably and reproducibly modulated valence and arousal. Accepted measures of valence and arousal in monkeys (autonomic) and humans (reported ratings) were used. FIG. 19A depicts human subject valence ratings of a series of images with two example images, in accordance with some embodiments described herein. The distribution of human valence ratings (1-7) is shown for a group of 900 images.

Figures 19B, 19C:
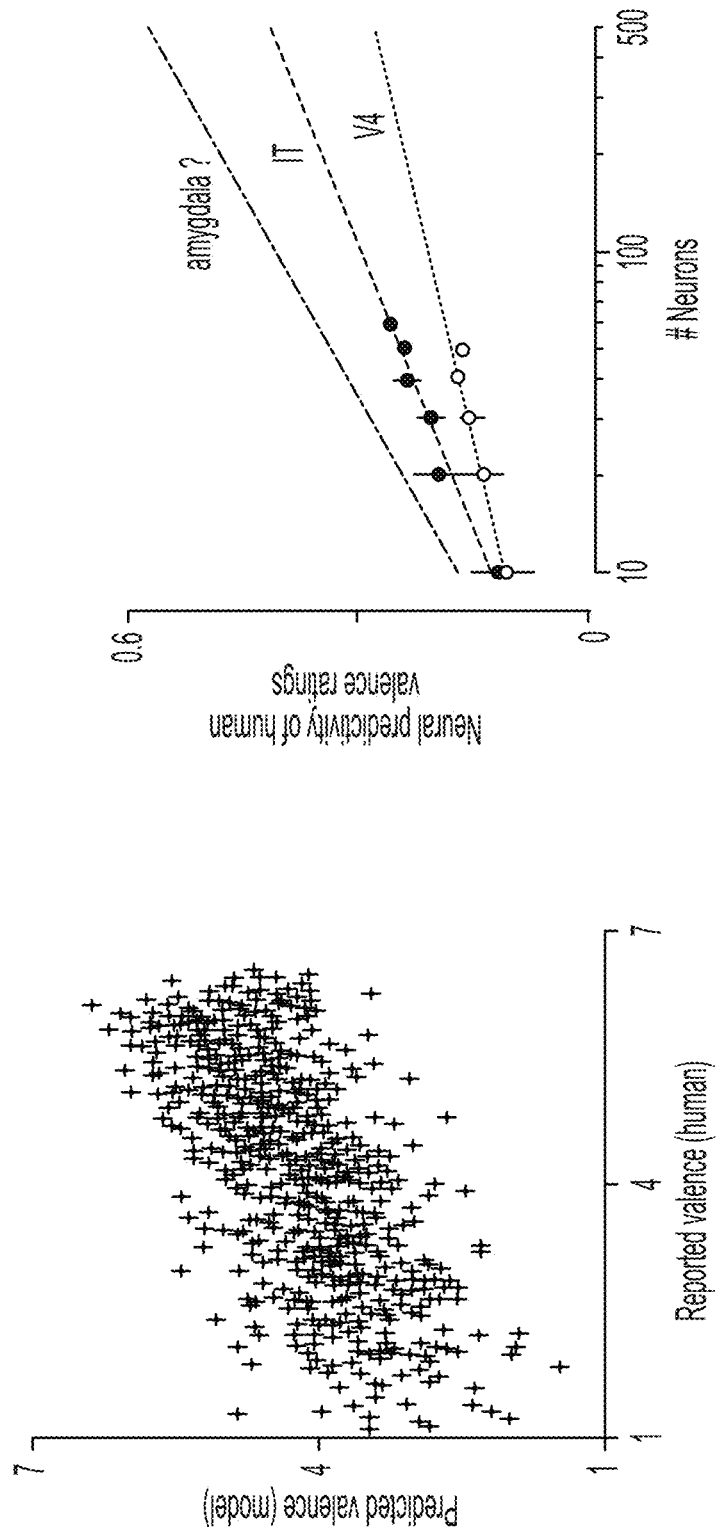
FIG. 19B is a prediction of human valence ratings by an ANN model, in accordance with some embodiments described herein.
FIG. 19C are cross-validated predictions of human valence ratings by recorded IT neural population responses, recorded V4 population responses, and hypothesized basolateral amygdala as a function of population size, in accordance with some embodiments described herein.

Preliminary results show that the existing ANN models are able to reasonably capture these two major dimensions of emotional affect. FIG. 19B shows a prediction of human valence ratings by one ANN model for the IT population: regressed on (heldout) human data (Pearson R=0.7; p<0.0001). FIG. 19C are cross-validated predictions of human valence ratings by recorded IT neural population responses, recorded V4 population responses, and hypothesized basolateral amygdala as a function of population size, in accordance with some embodiments described herein. These results open the possibility of finding images that might be underlying neural activity (especially for the amygdala) to population activity patterns that appear unlikely to be visited by natural images. One of these with potential clinical relevance is high positive valence, but low arousal.

V. Methods

A. Electrophysiological Recordings in Macaques

Neural sites across the macaque V4 cortex were sampled and recorded in the left, right, and left hemisphere of three awake, behaving macaques, respectively. In each monkey, one chronic 96-electrode microelectrode array (Utah array) was implanted immediately anterior to the lunate sulcus (LS) and posterior to the inferior occipital sulcus (IOS), with the goal of targeting the central visual representation (<5° eccentricity, contralateral lower visual field). Each array sampled from ~25 mm$^2$ of dorsal V4. On each day, recording sites that were visually-driven as measured by response correlation ($r_{Pearson}$>0.8) across split-half trials of a fixed set of 25 out-of-set naturalistic images shown for every recording session (termed, the normalizer image set) were deemed "reliable."

It was not assumed that each V4 electrode was recording only the spikes of a single neuron. Hence the term neural "site" is used herein. But it was required that the spiking responses obtained at each V4 site maintained stability in its image-wise "fingerprint" between the day(s) that the mapping images were tested (e.g., the response data used to build the ANN-driven predictive model of each site) and the days that the Controller images or the complex curvature images were tested. Specifically, to be "stable," it was required that an image-wise Pearson correlation of at least 0.8 in its responses to the normalizer set across recording days. Neural sites that were reliable on the experimental mapping day and the experimental test days, and were stable across all those days, were termed "validated." All validated sites were included in all presented results. To avoid any possible selection biases, this selection of validated sites was done on data that were completely independent from the main experimental result data. In total, 107 validated V4 sites were recorded from during the ANN-mapping day which included 52, 33 and 22 sites in monkey-M (left hemisphere), monkey-N (right hemisphere), and monkey-S (left hemisphere), respectively. Of these sites, 76 of were validated for the stretch control experiments ($n_M$=38, $n_N$=19, $n_S$=19) and 57 were validated for the one-hot population control experiments ($n_M$=38, $n_S$=19).

To allow meaningful comparisons across recording days and across V4 sites, the raw spiking rate of each site from each recording session was normalized (within just that session) by subtracting its mean response to the 25 normalizer images and then dividing by the standard deviation of its response over those normalizer images (these are the arbitrary units shown as firing rates in FIGS. 6A, 7A, and 8). The normalizer image set was always randomly interleaved with the main experimental stimulus set(s) run on each day.

Control experiments consisted of three steps. In the first step, neural responses were recorded to our set of naturalistic images that were used to construct the mapping function between the ANN activations and the recorded V4 sites. In a second, offline step, these mapping functions (e.g., a predictive model of the neural sites) were used to synthesize the controller images. Finally in step three, the neural responses to the synthesized images were recorded. The time between step 1 and step 3 ranged from several days to 3 weeks.

B. Fixation Task

All images were presented while monkeys fixated on a white square dot (0.2°) for 300 ms to initiate a trial. A sequence of 5 to 7 images was then presented, each ON for 100 ms followed by a 100 ms gray blank screen. This was followed by a water reward and an inter-trial interval of 500 ms, followed by the next sequence. Trials were aborted if gaze was not held within +0.5° of the central fixation dot during any point. To estimate the classical receptive field (cRF) of each neural site, 1°×1° white squares were flashed across the central 8° of the monkeys' visual field, measured the corresponding neural responses, and then fitted to a 2D Gaussian to the data. 1-std was defined as the cRF of each neural site.

C. Naturalistic Image Set

A large set (N=640) of naturalistic images was used to measure the response of each recorded V4 neural sites and every model V4 neural site to each of these images. Each of these images contained a three-dimensional rendered object instantiated at a random view overlaid on an unrelated natural image background.

D. Complex Curvature Stimuli

A set of images including closed shapes constructed by combining concave and convex curves was used. These stimuli are constructed by parametrically defining the number and configuration of the convex projections that constituted the shapes. Previous experiments with these shapes showed that curvature and polar angle were quite good at describing the shape tuning. The number of projections varied between 3 to 5 and the angular separation between projections was in 45° increments. These shapes were previously shown to contain good drivers of V4 neurons of macaque monkeys. The complex curve images were generated using the code generously supplied by the authors of that prior work. The stimuli were presented at the center of the receptive field of the neural sites.

E. Cross-Validation Procedure for Evaluating Control Scores

To evaluate the scores from the neural responses to an image set, the neural response repetitions were divided into two, randomly-selected halves. The mean firing rate of each neural site in response to each image was then computed for each half. The mean responses from the first half were used to find the image that produces the highest score (in that half) and the response to that image is then measured in the second half (and this is the measurement used for further analyses). This procedure 50 times was repeated for each neural site (e.g., 50 random half splits). For stretch and one-hot population experiments the score functions were the "neural firing rate" and "softmax score" respectively. Each score for the synthetic controller images and for the reference images was computed (either the naturalistic or the complex curvature sets). The synthetic "gain" in the control score was calculated as the difference between the synthetic controller score and the reference score, divided by the reference score.

F. V4 encoding model

To use the ANN model to predict each recorded neural site (or neural population), the internal V4-like representation of the model may first be mapped to the specific set of recorded neural sites. The assumptions behind this mapping are discussed elsewhere, but the key idea is that any good model of a ventral stream area may contain a set of artificial neurons (a.k.a. features) that, together, span the same visual encoding space as the brain's population of neurons in that area (e.g., the model layer must match the brain area up to a linear mapping). To build this predictive map from model to brain, a specific deep ANN model with locked parameters was used. Herein, a variant of Alexnet architecture trained on Imagenet was used as it has previously been found that the feature space at the output of the Conv-3 layer of Alexnet to be a good predictor of V4 neural responses. During training, the middle convolutional layers were not split between GPUs.

In addition, the input images were transformed using an eccentricity-dependent function that mimics the known spatial sampling properties of the primate retinac. We termed this the "retinae transformation." It had previously been found that training deep convolutional ANN models with retinae-transformed images improves the neural prediction accuracy of V4 neural sites (an increase in explained variance by ~5-10%). The "retina transformation" was implemented by a fish-eye transformation that mimics the eccentricity-dependent sampling performed in primate retinae. All input images to the neural network were preprocessed by randomly cropping followed by applying the fish-eye transformation. Parameters of the fish-eye transformation were tuned to mimic the cones density ratio in fovea at 4° peripheral vision.

The responses of the recorded V4 neural sites in each monkey and the responses of all the model "V4" neurons were used to build a mapping from model to the recorded population of V4 neural sites (FIGS. 5A-5E). A convolutional mapping function that significantly reduces the neural prediction error compared to other methods like principal component regression was used. The implementation was a variant of a 2-stage convolutional mapping function in which the group sparsity regularization term was substituted with an L2 loss term to allow for smooth (non-sparse) feature mixing. The first stage of the mapping function comprises a learnable spatial mask ($W_s$) that is parameterized separately for each neural site (n) and is used to estimate the receptive field of each neuron. The second stage comprises a mixing point-wise convolution ($W_d$) that computes a weighted sum of all feature maps at a particular layer of the ANN model (Conv3 layer, herein). The mixing stage finds the best combination of model features that are predictive of the each neural sites response. The final output is then averaged over all spatial locations to form a scalar prediction of the neural response. Parameters are jointly optimized to minimize the prediction error $\mathcal{L}_e$ on the training set regularized by combination of $\mathcal{L}_2$ and smoothing Laplacian losses, $\mathcal{L}_{Laplace}$ (defined below). By factorizing the spatial and feature dimensions, this method significantly improves the predictivity of neural responses over the traditional principle component regression. This improved predictive power is interpreted to be resulting from the fact that it imposes a prior on the model-to-brain mapping procedure which is strongly in line with an empirical fact: that each neuron in area V4 has a receptive field. That neuron is thus best explained by linear combinations of simulated neurons that have similar receptive fields.

$$\hat{y}_n = \left(\sum \left(W_s^{(n)} \cdot X\right)\right) \cdot W_d^{(n)} + w_b^{(n)} \qquad (1)$$

$$\mathcal{L}_2 = \lambda_s \sum_n W_s^{(n)2} + \lambda_d \sum_n W_d^{(n)2} \qquad (2)$$

$$\mathcal{L}_{Laplace} = \lambda_s \sqrt{\sum_n \left(W_s^{(n)2} * L\right)^2}, \quad L = \begin{bmatrix} 0 & -1 & 0 \\ -1 & 4 & -1 \\ 0 & -1 & 0 \end{bmatrix} \qquad (3)$$

$$\mathcal{L}_e = \sqrt{\sum_n (\hat{y}_n - y)^2} \qquad (4)$$

$$\mathcal{L} = \mathcal{L}_e + \mathcal{L}_{Laplace} + \mathcal{L}_2 \qquad (5)$$

The model was evaluated using 2-fold cross-validation and observed that ~89% of the explainable variance could be explained with our model in three monkeys (EVM=92%, EVN=92%, EVS=80%). The addition of the retinae transformation together with the convolutional mapping function increased the explained variance by ~13% over the naive principal component regression applied on features from the model trained without the retinae transformation (EVM=75%, EVN=80%, EVS=73%). Ablation studies on data from each monkey suggested that on average about 3-8% of the improvements were due to the addition of the retinae transformation (see Table 1). For constructing the final mapping function, adopted for image synthesis, the mapping function parameters were optimized on 90% of the data, selected randomly.

The resulting predictive model of V4 (ANN features plus linear mapping) is referred to as the mapped V4 encoding model and, by construction, it produces the same number of artificial V4 "neurons" as the number of recorded V4 neural sites (52, 33, and 22 neural sites in monkeys M, N and S respectively).

TABLE 1

Median prediction accuracy over all measured neural sites in three monkeys using different mapping methods and model features. Addition of the Retinae transformation and convolutional mapping account for 3-8% and 5-9% of the improvement in prediction accuracy compared to the principle component regression method respectively.

|  | Mapping Type | Model Type | Median Normalized EV (%) |
| --- | --- | --- | --- |
| Monkey-M | PCR | Conv3 | 80 |
|  | Klindt et al. | Conv3 | 88 |
|  | Klindt et al. | Retinae-Conv3 | 92 |
| Monkey-N | PCR | Conv3 | 75 |
|  | Klindt et al. | Conv3 | 84 |
|  | Klindt et al. | Retinae-Conv3 | 92 |
| Monkey-S | PCR | Conv3 | 72 |
|  | Klindt et al. | Conv3 | 77 |
|  | Klindt et al. | Retinae-Conv3 | 80 |

G. Retinae Transformation

To retain the resolution of the retinae-transformed images as high as possible, the input image was not subsampled with a fixed sampling pattern. Instead, the implementation of the retinae sampling utilizes a backward function $r=g(r')$ that maps the radius of points in the retinae transformed image (r') to those in the input image (r). In this way, for every pixel in the output image, the corresponding pixel in the input image can be found using the pixel-mapping function g. To formulate the pixel-mapping function, g, the known rate of change of cones density ($\rho$) in the primate retinae may be used, as it exponentially decreases with eccentricity.

$$\rho = \frac{1}{\pi d^2} = e^{-ar'} \tag{6}$$

where d is the distance between nearby cones and r' is the radial distance from the fovea in the transformed image. From this, one can write d as a function of r'.

$$d = \frac{1}{\sqrt{\pi}} = e^{ar'/2} \tag{7}$$

The ratio between the cones density in the fovea and the outmost periphery given the specific visual field size in which the stimulus has been presented in the experiment could be written as:

$$\frac{\rho_f}{\rho_p} = e^{ar'_{max}} \tag{8}$$

where $\rho_f$ and $\rho_p$ are the cone densities at the fovea and periphery respectively, and $r'_{max}$ is the highest radial distance in the output image (e.g. 150 for an image of size 300). From equation (8) above one can calculate a as a function of $\rho_f$, $\rho_p$, and $r'_{max}$.

$$a = \frac{\ln \frac{\rho_f}{\rho_p}}{r'_{max}} \tag{9}$$

The $\rho_f/\rho_p$ ratio is known given the size of the visual field in which the stimuli were presented (e.g. 10 for fovea to 4-degrees in this study) and the output image size (e.g. 150 in this study). One can now formulate the function g(r') as the sum of all the distances d up to radius r' weighted by a factor b.

$$g(r') = \frac{b}{\sqrt{\pi}} \sum_{k=0}^{r'-1} d_k = \frac{b}{\sqrt{\pi}} \sum_{k=0}^{r'-1} e^{ar/2} = \frac{b}{\sqrt{\pi}} \frac{1-e^{ar'/2}}{1-e^{a/2}} \tag{10}$$

where b is found so that $$\frac{r_{max}}{g(r'_{max})} = 1.$$

In this implementation the Brents method was used to find the optimal b value.

H. Finding the Best Representation in the ANN Model

Figure 17A:
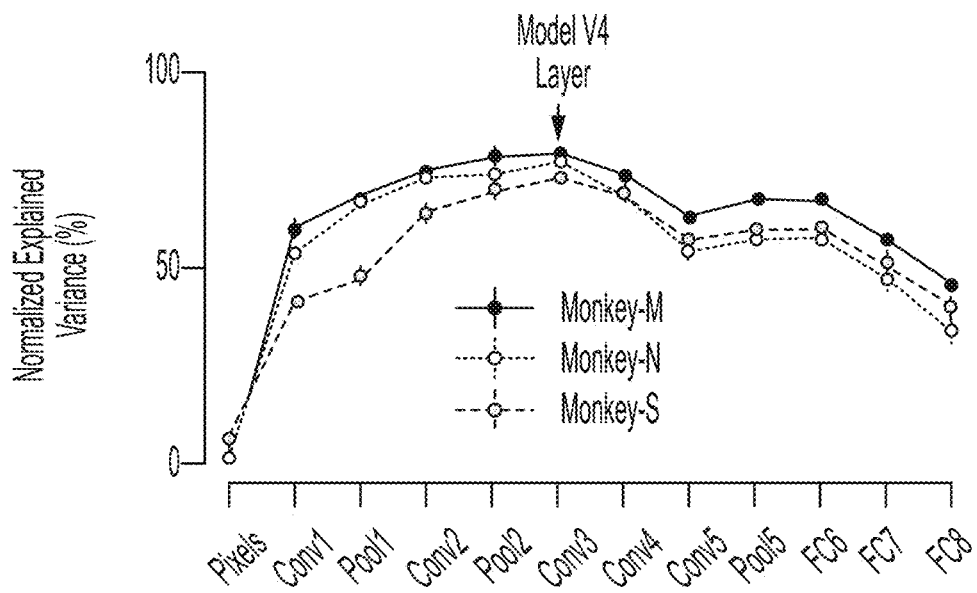
FIG. 17A depicts normalized explained variance for stimulus images at each layer of the deep ANN model for three subjects, in accordance with some embodiments described herein.

Linear mapping from model features to neural measurements was used to compare the representation at each stage of processing in the ANN model. For features in each layer of the ANN model, principal component analysis was applied to extract the top 640 dimensions. A linear transformation was then fitted to the data using a Ridge regression method and computed the amount of explained variance (EV) by the mapping function. For each neural site the EV was normalized by the internal consistency of measurements across repetitions. The median normalized EV across all measured sites was used to select the best representation in the ANN model. FIG. 17A depicts normalized explained variance for stimulus images at each layer of the deep ANN model for three subjects, in accordance with some embodiments described herein. The ANN features at the output of each layer may be used to predict the measurements from V4 sites. The amount of explained variance by these features is normalized by the internal consistency of neurons across stimulus presentations.

The similarity of representations at each layer of the ANN model and the neural measurements were quantified using the image-level representational dissimilarity matrix (RDM) that followed the same pattern as that which was obtained from linear mapping method.

Figure 17B:
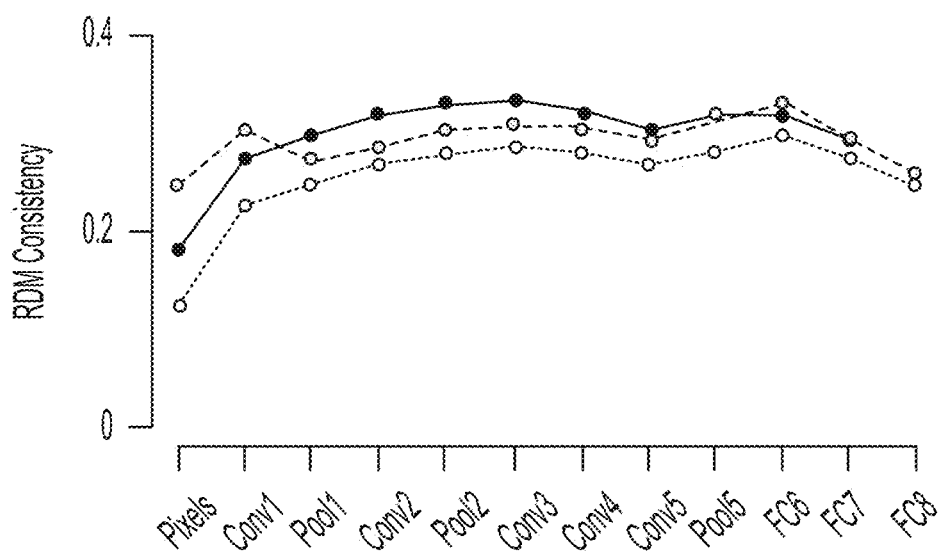
FIG. 17B depicts calculated Pearson correlation values of the image-level representational dissimilarity matrix for stimulus images at each layer of the deep ANN model for three subjects, in accordance with some embodiments described herein.

RDMs were computed using the principle components of the features at each layer in response to the naturalistic image set (n=640). FIG. 17B depicts calculated Pearson correlation values of the image-level representational dissimilarity matrix for stimulus images at each layer of the deep ANN model for three subjects, in accordance with some embodiments described herein. The consistency between V4 representation (spanned by the measured neural responses) and representations at each layer of the ANN model is quantified by constructing the image-level RDM for each one and computing the Pearson correlation between the elements in the upper-triangle of the two matrices.

I. Synthesized "Controller" Images

The "response" of artificial neuron in the mapped V4 encoding model (above) is a differentiable function of the pixel values $f: \mathcal{J}^{w \times h \times c} \to \mathbb{R}^n$ that enables the use of the model to analyze the sensitivity of neurons to patterns in the pixels space. The synthesis operation may be formulated as an optimization procedure during which images are synthesized to control the neural firing patterns in the following two settings:

1. Stretch: Controller images are synthesized to attempt to push each individual V4 neural site into its maximal activity state. To do so, the controller iteratively changes the pixel values in the direction of the gradient that maximizes the firing rate of the corresponding model V4 neural site. The procedure was repeated for each neural site using five different random starting images, thereby generating five "stretch" controller images for each V4 neural site.
2. One Hot Population: Similar to the "stretch" scenario, except that here the optimization was selected to change the pixel values in a way that (i) attempts to maximize firing rate of the target V4 neural site, and (ii) attempts to maximally suppress the firing rates of all other recorded V4 neural sites. The one-hot population goal is formalized in the following objective function that is then aimed to maximize during the image synthesis procedure:

$$S = \text{Softmax}_t(y) = \frac{e^{y_t}}{\sum e^{y_i}} \quad (11)$$

where t is the index of the target neural site, and $y_i$ is the response of the model V4 neuron i to the synthetic image.

Each optimization run begins with an image that consists of random pixel values drawn from a standard Normal distribution and then optimizes the objective function for a pre-specified number of steps using a gradient ascend algorithm (steps=700). The total variation (defined below) may also be used as additional regularization in the optimization loss to reduce the high frequency noise in the generated images:

$$L_{TV} = \sum_{i,j}(\|I_{i+1,j} - I_{j}\|_2 + \|I_{:,j+1} - I_{i,j}\|_2) \quad (12)$$

During the experiments, the monkeys may be required to fixate within a 1° circle at the center of the screen. This introduces an uncertainty on the exact gaze location. For this reason, images are synthesized to be robust to small translations of maximum 0.5°. At every iteration, the image is translated in random directions (i.e. jittering) with a maximum translation length of 0.5° in each direction, thereby generating images that are predicted to elicit similarly high scores regardless of the translations within the range. The total-variation loss and the translation-invariance procedure reduce the amount of high-frequency noise patterns in the generated images commonly known as adversarial examples. In addition, at every iteration during the synthesis procedure, the computed gradients may be normalized by its global norm and the pixel values may be clipped at −1 and 1.

J. Contrast Energy

It has been shown that neurons in area V4 may respond more strongly to higher contrast stimuli. To ask if contrast energy (CE) was the main factor in "stretching" the V4 neural firing rates, the CE was computed within the receptive field of the neural sites for all the synthetic and the classic V4 stimuli. CE was calculated as the ratio between the maximum and background luminances. For all images, the average luminance was used as the background value. Because the synthetic images consisted of complex visual patterns, the CE was also computed using an alternative method based on spectral energy within the receptive field. The average power was computed in the cRF in the frequency range of 1-30 cycles/degree. For all tested neural sites, the CE within the cRF for synthetic stretch controller images was less than or equal to the classic, complex curvature V4 stimuli (e.g., FIGS. 13A and 13B).

K. cRF-Cropped Contrast-Matched Naturalistic Stimuli

For each neural site, a new naturalistic image-set was first produced by cropping the older naturalistic image-set at the estimated cRF of the respective site. The contrast of these naturalistic images was matched (within the cRF of that neuron) to the average contrast across all five synthesized images (generated for the same neural site). The predicted neural responses to all these new cRF-masked, contrast matched naturalistic images was computed and the stretch control gain achieved with this set over the original naturalistic images was evaluated. The stretch control gain using these images showed a 14% decrease in the median gain over all target neurons. This meant that the original naturalistic image-set without the cRF masking and contrast-matching contained better drivers of the neural sites measured in our experiments. Masking the images with the estimated cRF was responsible for most of the drop in the observed stretch control gain (11%; see FIG. 16). The contrast energy within the cRF was higher for best naturalistic images compared to synthetic images for most sites (median ratio of synthetics contrast to best naturalistic images was 0.76 over all tested sites).

L. Monte-Carlo Mask Optimization

The mask parameters formulated as a 2-D Gaussian function (i.e. mu, sigma1, sigma2, rho) were estimated for each neural site via Monte-Carlo simulations (n=500). Each parameter was sampled from the corresponding distribution derived from the measured neural sites in each monkey. For each Monte-Carlo simulation, the mask parameters were sampled from the above-mentioned distributions and constructed a 2-D mask. The naturalistic images were masked with the sampled mask (cropped at 1-SD) and image contrasts were matched to the average contrast of synthetic images produced for each neural site within the mask. For each neural site, the mask parameters were selected that elicited the maximum average firing rate (predicted) across all images in the naturalistic set. The maximum predicted output for each neural site in response to these images was used to evaluate the stretch control gain that showed a non-significant gain over the naturalistic images.

M. Affine Transformations of the Naturalistic Image-Set

There might be simple image transformations that could achieve the same level of control as that obtained by the synthetic images. To test this, an additional analysis was conducted in which the best naturalistic image for each neural site was randomly transformed using various affine transformations (e.g., translation, scale, and rotation; n=100) and calculated the predicted responses to those images. Four experiments were considered with the following transformations used in each one: 1) random scaling between 0.5 to 2; 2) random translation between −25 to 25 pixels in each direction; 3) random rotation between 0 to 90 degrees; and 4) mixture of all three transformations. For each experiment, the stretch control gain was evaluated over the naturalistic image set achieved with these new images that showed significantly lower gains for all of the alternative methods compared to our proposed model-based method (see FIG. 16).

N. Combining Best Driver Images

Images that are good drivers of the measured neurons could be combined together to form new mixed images that might drive the neurons even further. To test this hypothesis, the top naturalistic images for each neuron were combined by taking the average pixel value over all select images and matched the contrast (within cRF of each neural site) of the mixed image to the average contrast across synthetic images generated for each neuron. Various number of top images were tried to create the mixed image (i.e. top-2, 3, 4, and 5). The predicted stretch control gain using these mixed images over the naturalistic image set was computed and it was found that these images were considerably weaker drivers of the same neurons (see FIG. 16).

O. Quantifying the novelty of synthetic images

A hypothesis was created that if the synthetic stimuli are indeed novel, they should be less similar (e.g., correlated) to any of the naturalistic images than the naturalistic images are to themselves. The distances between synthetic and naturalistic images were computed in pixel-space as well as in the space of neural responses. To test this, the minimum Euclidean distance was measured (in the space of measured neural responses) between each synthetic image and all naturalistic images and compared them with minimum distances obtained for naturalistic images. FIGS. 15A-15E show the distribution of minimum distances synthetic and naturalistic images to any naturalistic images and illustrates the point that the responses to synthetic images are significantly farther from the distribution of responses to naturalistic images than expected from sampling within the naturalistic space (FIGS. 15A, 15C, and 15E) or by applying simple image transformations on images sampled from that space (FIGS. 15B and 15D). Therefore, these images can quantifiably be described as out-of-domain (Wilcoxon rank-sum test; $Z(3798)=30.8$; $p<0.0001$). The distances between synthetic and naturalistic images in the pixel space were also computed using the correlation distance $(1-\rho)$ and showed a similar distinction between the two (Wilcoxon rank-sum test; $Z(37120)=29.3$; $p<0.0001$). FIG. 15F shows a scatter plot of 640 naturalistic images (open circles) and 285 synthetic images (filled circles) where the axes are the first two principle components of the measured V4 population response space (data from monkey-S).

Techniques operating according to the principles described herein may be implemented in any suitable manner. Included in the discussion above are a series of flow charts showing the steps and acts of various processes that non-invasively control targeted neural activity. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application, for example as a software program application such as stimulus generation facility 122 of FIG. 1. In other implementations, the functional facilities may be adapted to interact with other functional facilities in such a way as form an operating system, including the Windows® operating system, available from the Microsoft® Corporation of Redmond, Washington. In other words, in some implementations, the functional facilities may be implemented alternatively as a portion of or outside of an operating system.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as computer-readable storage media 806 of FIG. 8 described below (i.e., as a portion of a computing device 800) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

Figure 20:
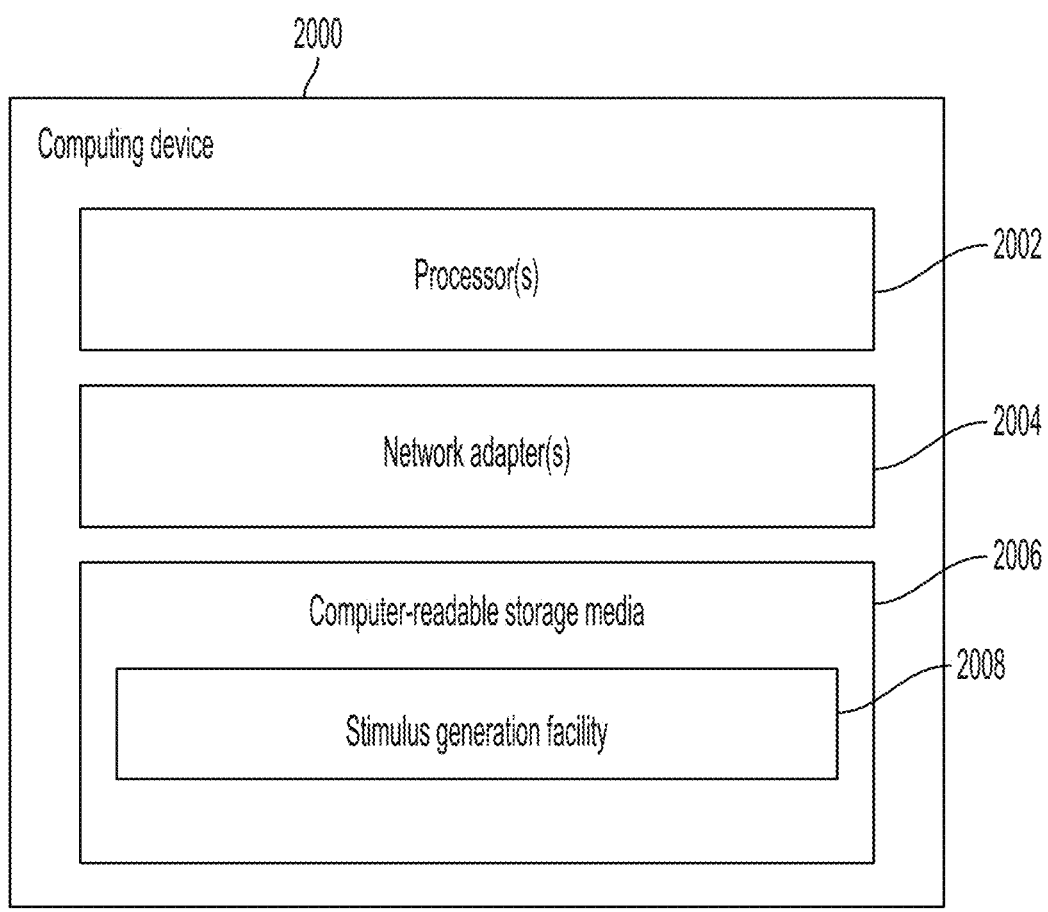
FIG. 20 is a schematic diagram of an illustrative computing device with which aspects described herein may be implemented.

In some, but not all, implementations in which the techniques may be embodied as computer-executable instructions, these instructions may be executed on one or more suitable computing device(s) operating in any suitable computer system, including the exemplary computer system of FIG. 20, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, a computer-readable storage medium accessible via one or more networks and accessible by the device/processor, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing devices (co-located or geographically distributed) dedicated to executing the techniques described herein, one or more Field-Programmable Gate Arrays (FPGAs) for carrying out the techniques described herein, or any other suitable system.

FIG. 20 illustrates one exemplary implementation of a computing device in the form of a computing device 2000 that may be used in a system implementing techniques described herein, although others are possible. It should be appreciated that FIG. 20 is intended neither to be a depiction of necessary components for a computing device to operate as a stimulus system console in accordance with the principles described herein, nor a comprehensive depiction.

Computing device 2000 may comprise at least one processor 2002, a network adapter 2004, and computer-readable storage media 2006. Computing device 2000 may be, for example, a desktop or laptop personal computer, a personal digital assistant (PDA), a smart mobile phone, a server, a wireless access point or other networking element, or any other suitable computing device. Network adapter 2004 may be any suitable hardware and/or software to enable the computing device 2000 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 2006 may be adapted to store data to be processed and/or instructions to be executed by processor 2002. Processor 2002 enables processing of data and execution of instructions. The data and instructions may be stored on the computer-readable storage media 2006.

The data and instructions stored on computer-readable storage media 2006 may comprise computer-executable instructions implementing techniques which operate according to the principles described herein. In the example of FIG. 20, computer-readable storage media 2006 stores computer-executable instructions implementing various facilities and storing various information as described above. Computer-readable storage media 2006 may store stimulus generation facility 2008 and/or generated stimulus inputs.

While not illustrated in FIG. 20 a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including." "comprising." "having." "containing." "involving." and variations thereof herein, is meant to encompass the items listed thereafter and equivalents thereof as well as additional items.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example unless otherwise indicated.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

What is claimed is:

1. A method of controlling targeted neural activity of a subject, the method comprising:
generating a stimulus input image configured to control targeted neural activity of the subject, the generating comprising:
mapping neural activity of a brain region of the subject to a deep artificial neural network (ANN) model, wherein the neural activity is responsive to presenting one or more naturalistic images to the subject;
generating an initial image comprising random pixel values;
masking the initial image with a receptive field of a neuron of the brain region of the subject to form a masked image; and
using the deep ANN model to synthesize the stimulus input image based on the masked image; and
applying the generated stimulus input image to retinae of the subject.

2. The method of claim 1, wherein using the deep ANN model to synthesize the stimulus input image comprises minimizing a loss function of the deep ANN model by iteratively changing pixel values within a receptive field of the masked image to synthesize the stimulus input image.

3. The method of claim 1, wherein mapping neural activity further comprises using a convolutional mapping function to map neural sites of the brain region of the subject to the deep ANN model.

4. The method of claim 3, wherein using the deep ANN model to synthesize the stimulus input image comprises minimizing a loss function of the deep ANN model by iteratively changing pixel values within a receptive field of the masked image to increase a firing rate of a neural site of the deep ANN model.

5. The method of claim 4, wherein minimizing the loss function of the deep ANN model further comprises iteratively changing pixel values within the masked receptive field of the masked image to reduce a firing rate of other neural sites of the deep ANN model.

6. The method of claim 1, further comprising recording neural responses from areas of a brain of the subject in response to applying the generated stimulus input image, wherein the areas of the brain are devoted to visual information processing.

7. The method of claim 6, wherein recording neural responses from the areas of the brain of the subject comprises recording neural responses from area V4 of the brain of the subject.

8. A system for controlling targeted neural activity of a subject, the system comprising:
at least one processor;
a non-transitory computer-readable storage medium storing instructions that, when executed by the at least one processor, cause the at least one processor to:
generate a stimulus input image configured to control targeted neural activity of the subject, the generating comprising:
mapping neural activity of a brain region of the subject to a deep artificial neural network (ANN) model, wherein the neural activity is responsive to presenting one or more naturalistic images to the subject;
generating an initial image comprising random pixel values;
masking the initial image with a receptive field of a neuron of the brain region of the subject to form a masked image; and
using the deep ANN model to synthesize the stimulus input image based on the masked image; and
an apparatus, coupled to the at least one processor, configured to apply the stimulus input image to retinae of the subject.

9. The system of claim 8, wherein using the deep ANN model to synthesize the stimulus input image comprises minimizing a loss function of the deep ANN model by iteratively changing pixel values within a receptive field of the masked image to synthesize the stimulus input image.

10. The system of claim 8, wherein mapping neural activity further comprises using a convolutional mapping function to map neural sites of the brain region of the subject to the deep ANN model.

11. The system of claim 10, wherein using the deep ANN model to synthesize the stimulus input image comprises minimizing a loss function of the deep ANN model by iteratively changing pixel values within a receptive field of the masked image to increase a firing rate of a neural site of the deep ANN model.

12. The system of claim 11, wherein minimizing the loss function of the deep ANN model further comprises iteratively changing pixel values within the masked receptive field of the masked image to reduce a firing rate of other neural sites of the deep ANN model.

13. The system of claim 8, wherein the instructions further cause the at least one processor to record neural responses from areas of a brain of the subject in response to applying the generated stimulus input image, wherein the areas of the brain are devoted to visual information processing.

14. The system of claim 13, wherein recording neural responses from areas of the brain of the subject comprises recording neural responses from area V4 of the brain of the subject.

15. A non-transitory computer-readable storage medium storing instructions that, when executed by at least one processor, cause the at least one processor to perform a method of controlling targeted neural activity of a subject, the method comprising:
generating a stimulus input image configured to control targeted neural activity of the subject, the generating comprising:
mapping neural activity of a brain region of the subject to a deep artificial neural network (ANN) model, wherein the neural activity is responsive to presenting one or more naturalistic images to the subject;

generating an initial image comprising random pixel values;

masking the initial image with a receptive field of a neuron of the brain region of the subject to form a masked image; and using the deep ANN model to synthesize the stimulus input image based on the masked image; and applying the generated stimulus input image to retinae of the subject.

16. The non-transitory computer-readable medium of claim 15, wherein using the deep ANN model to synthesize the stimulus input image comprises minimizing a loss function of the deep ANN model by iteratively changing pixel values within a receptive field of the masked image to synthesize the stimulus input image.

17. The non-transitory computer-readable medium of claim 15, wherein mapping neural activity further comprises using a convolutional mapping function to map neural sites of the brain region of the subject to the deep ANN model.

18. The non-transitory computer-readable medium of claim 17, wherein using the deep ANN model to synthesize the stimulus input image comprises minimizing a loss function of the deep ANN model by iteratively changing pixel values within a receptive field of the masked image to increase a firing rate of a neural site of the deep ANN model.

19. The non-transitory computer-readable medium of claim 18, wherein minimizing the loss function of the deep ANN model further comprises iteratively changing pixel values within the masked receptive field of the masked image to reduce a firing rate of other neural sites of the deep ANN model.

20. The non-transitory computer-readable medium of claim 15, wherein the method further comprises recording neural responses from areas of a brain of the subject in response to applying the generated stimulus input image, wherein the areas of the brain are devoted to visual information processing.

* * * * *